(12) United States Patent
Marasco et al.

(10) Patent No.: US 7,786,269 B2
(45) Date of Patent: Aug. 31, 2010

(54) ANTIBODY TO LATENT MEMBRANE PROTEINS AND USES THEREOF

(75) Inventors: Wayne A. Marasco, Wellesley, MA (US); Francesca Gennari, London (GB)

(73) Assignee: Dana-Farber Cancer Institute, Inc., Boston, MA (US)

(*) Notice: Subject to any disclaimer, the term of this patent is extended or adjusted under 35 U.S.C. 154(b) by 1135 days.

(21) Appl. No.: 10/496,861

(22) PCT Filed: Dec. 4, 2002

(86) PCT No.: PCT/US02/38849

§ 371 (c)(1), (2), (4) Date: Nov. 15, 2004

(87) PCT Pub. No.: WO03/048337

PCT Pub. Date: Jun. 12, 2003

(65) Prior Publication Data

US 2005/0129701 A1 Jun. 16, 2005

Related U.S. Application Data

(60) Provisional application No. 60/337,294, filed on Dec. 4, 2001.

(51) Int. Cl.
*A61K 39/395* (2006.01)
*A61K 39/00* (2006.01)
*A61K 39/42* (2006.01)
*A61K 35/14* (2006.01)
*C07K 14/00* (2006.01)
*C07K 16/00* (2006.01)
*A61K 39/145* (2006.01)

(52) U.S. Cl. ............... 530/387.3; 424/130.1; 424/133.1; 424/229.1; 424/141.1; 424/159.1; 530/350; 530/387.1; 530/386; 530/388.3

(58) Field of Classification Search .......................... None
See application file for complete search history.

(56) References Cited

U.S. PATENT DOCUMENTS

| 6,642,008 | B1* | 11/2003 | Harley et al. ............ 435/7.1 |
| 6,699,971 | B2* | 3/2004 | Birkenbach et al. ...... 530/387.1 |
| 2001/0034432 | A1 | 10/2001 | Sodroski et al. |
| 2006/0068442 | A1* | 3/2006 | Middeldorp ............... 435/6 |

FOREIGN PATENT DOCUMENTS

| EP | 1 229 043 | 8/2002 |
| WO | WO 93/19163 | 9/1993 |
| WO | WO 97/15669 A | 5/1997 |
| WO | WO 01/37868 A | 5/2001 |
| WO | WO 02/060930 | * 8/2002 |

OTHER PUBLICATIONS

Mirzabekov, T. et al., Nature Biotechnology, 18:649-654 (2000).
Harrison, J. L. et al., "Screening of Phage Antibody Libraries," Methods in Enzymology 267:83-109, 1996.
Mhashilkar, A. M. et al., "Inhibition of HIV-1 Tat-mediated LTR . . . " EMBO Journal 14(7):1542-1551, 1995.
Kenney et al., "Antisense to the Epstein-Barr Virus (EBV)-Encoded Latent Membrane Protein 1 (LMP-1) Sensitizes EBV-Immortalized B Cells to Transforming Growth Factor-Beta and Chemotherapeutic Agents," *Int. J. Cancer*, 91:89-98 (2001).
Maruoka et al., "Detection of Epstein-Barr Virus in Warthin's Tumor," *J. Tokyo Wom. Med. Univ.*, 71(2):99-106 (2001).
Mattia et al., "Inhibition of in vitro Proliferation of Epstein Barr Virus Infected B Cells by an Antisense Oligodeoxynucleotide Targeted Against EBV Latent Membrane Protein LMP1," *Oncogene*, 15:489-493 (1997).
Meij et al., Restricted low-level human antibody responses against Epstein-Barr virus (EBV)-encoded Latent membrane protein 1 in a subgroup of patients with EBV-associated diseases, *J Infect. Dis.*, 179:1108-1115 (1999).
Jenski et al., "Docosahexaenoic Acid-Containing Phosphatidylcholine Affects the Binding of Monoclonal Antibodies to Purified K$^b$ Reconstituted into Liposomes," *Biochim. Biophys. Acta*, 1467:293-306 (2000).
Jesperson et al., "Use of Proteoliposomes to Generate Phage Antibodies Against Native AMPA Receptor," *Eur. J. Biochem.*, 267:1382-1389 (2000).
Laukkanen et al., "Lipid-Tagged Antibodies: Bacterial Expression and Characterization of a Lipoprotein-Single-Chain Antibody Fusion Protein," *Protein Engg.*, 6:449-454 (1993).
Lebowitz, David, "Epstein-Barr Virus and a Cellular Signaling Pathway in Lymphomas from Immunosuppressed Patients," *New Eng. J. Med.*, 338:1413-1421 (1998).
Meij et al., "Production Monitoring and Purification of EBV Encoded Latent Membrane Protein 1 Expressed and Secreted by Recombinant Baculovirus Infected Insect Cells," *J. Virol. Meth.*, 90:193-204 (2000).
Westerman, et al., "Protein Transfer of the Costimulatory Molecule, B7-2 (CD86), into Tumor Membrane Liposomes as a Novel Cell-Free Vaccine," *J. Immuno. Methods*, 236:77-87 (2000).
Xu et al., "Analysis and Significance of Anti-Latent Membrane Protein-1 Antibodies in the Sera of Patients with EBV-Associated Diseases," *J. Immunol.*, 164:2815-2822 (2000).

* cited by examiner

*Primary Examiner*—Zachariah Lucas
*Assistant Examiner*—Benjamin P Blumel
(74) *Attorney, Agent, or Firm*—Fish & Richardson P.C.

(57) ABSTRACT

The present invention provides antibodies and antibody fragments directed against extracellular domains of the EBV LMP proteins, including LMP1, LMP2A and LMP2B. The invention also provides methods of treating EBV-associated malignancies using these LMP specific antibodies.

10 Claims, 5 Drawing Sheets

| | 1 | 2 | 3 | 4 | 5 | 6 | 7 | 8 | 9 | 10 | 11 | 12 | |
|---|---|---|---|---|---|---|---|---|---|---|---|---|---|
| A | 3.4<br>1.6<br>1.4 | 2<br>3<br>1.2 | 1.7<br>1.7<br>2.4 | 2.4<br>2.4<br>2.4 | 0.9<br>2.8<br>2 | 4<br>2<br>2.5 | 1.3<br>1.9<br>2.6 | 3.8<br>2<br>2.3 | 1.1<br>1.3<br>1.5 | 2<br>1<br>1.3 | 3.1<br>1.6<br>3.8 | 1.8<br>1.5<br>2.5 | } WT4 (LMP1) |
| | 0.7<br>0.6<br>0.4 | 0.5<br>0.6<br>0.3 | 0.4<br>0.7<br>0.6 | 0.3<br>0.6<br>0.4 | 0.3<br>0.7<br>0.8 | 0.3<br>0.4<br>0.6 | 0.6<br>0.6<br>0.7 | 0.2<br>0.7<br>0.7 | 0.4<br>0.2<br>0.3 | 0.6<br>0.3<br>0.9 | 0.5<br>0.3<br>1 | 0.9<br>0.6<br>0.3 | } BJAB |
| | 13 | 14 | 15 | 16 | 17 | 18 | 19 | 20 | 21 | 22 | 23 | 24 | |
| B | 0.4<br>0.7<br>1.5<br>0.7 | 0.2<br>0.4<br>1.9<br>1 | 0.25<br>0.4<br>2<br>2 | 0.25<br>0.4<br>2<br>1 | 0.12<br>1<br>2.5<br>3 | 0.6<br>0.8<br>2.5<br>3 | 0.9<br>0.8<br>2.2<br>3.7 | 1.05<br>0.95<br>2.3<br>2.5 | 0.4<br>0.4<br>1.5<br>2.3 | 0.93<br>1.35<br>1.1<br>1.7 | 0.16<br>0.6<br>1<br>3.6 | 0.4<br>1.2<br>1.3<br>2 | } WT4 |
| | 0.3<br>0.5<br>0.4<br>0.1 | 0.2<br>0.5<br>0.5<br>0.6 | 0.3<br>0.5<br>0.6<br>0.4 | 0.16<br>0.6<br>0.9<br>0.3 | 0.2<br>0.3<br>0.9<br>0.5 | 0.3<br>0.3<br>0.6<br>0.6 | 0.36<br>0.4<br>0.7<br>0.7 | 0.12<br>0.8<br>0.1<br>0.8 | 0.3<br>0.5<br>0.5<br>0.5 | 0.12<br>0.3<br>0.4<br>0.8 | 0.1<br>0.5<br>0.3<br>1.5 | 0.1<br>0.5<br>0.4<br>0.3 | } BJAB |
| | 25 | 26 | 27 | 28 | 29 | 30 | 31 | 32 | 33 | 34 | 35 | 36 | |
| C | 0.3<br>1.1<br>1.4<br>0.9 | 0.25<br>0.4<br>0.8<br>0.4 | 0.63<br>0.69<br>2.3<br>2.2 | 0.6<br>0.9<br>2.7<br>1.3 | 0.43<br>1.55<br>2.9<br>2.2 | 1.8<br>2<br>2.1<br>3 | 0.58<br>1.44<br>1.5<br>2.9 | 0.8<br>2.5<br>2.5<br>2.7 | 0.8<br>0.43<br>0.6<br>2 | 1<br>3.2<br>2<br>2.5 | 0.2<br>0.6<br>1.2<br>4 | 0.5<br>0.8<br>1.2<br>3 | } WT4 |
| | 0.3<br>1.4<br>0.5<br>0.1 | 0.2<br>0.4<br>0.2<br>0.6 | 0.3<br>0.3<br>0.5<br>0.4 | 0.3<br>0.7<br>1.7<br>0.3 | 0.2<br>0.7<br>1<br>0.5 | 0.4<br>0.4<br>1<br>0.6 | 0.3<br>0.6<br>0.7<br>0.6 | 0.2<br>1<br>0.8<br>1.2 | 0.5<br>0.7<br>0.3<br>0.5 | 0.4<br>0.8<br>0.5<br>0.8 | 0.2<br>1.3<br>0.4<br>1.4 | 0.3<br>0.6<br>0.4<br>0.2 | } BJAB |
| | 37 | 38 | 39 | 40 | 41 | 42 | 43 | 44 | 45 | 46 | 47 | 48 | |
| D | 0.32<br>0.73<br>1.2<br>0.73 | 0.32<br>0.44<br>2<br>0.8 | 0.27<br>0.57<br>3<br>1.7 | 0.32<br>0.66<br>2.5<br>1.7 | 0.7<br>1.3<br>2.1<br>2 | 1.03<br>1.7<br>2.3<br>2.2 | 0.86<br>2.8<br>2.5<br>2 | 0.84<br>2.8<br>2.8<br>2.5 | 0.3<br>1.2<br>1.6<br>2.5 | 1.3<br>3.6<br>1.6<br>2.6 | 1.2<br>1.1<br>3.8<br>2.8 | 1<br>0.9<br>1.2<br>1.7 | } WT4 |
| | 0.3<br>0.7<br>0.5<br>0.1 | 0.3<br>0.4<br>0.4<br>0.4 | 0.5<br>0.5<br>0.3<br>0.5 | 0.4<br>0.9<br>0.8<br>0.4 | 0.2<br>0.6<br>0.8<br>0.7 | 0.3<br>0.5<br>0.8<br>2 | 0.6<br>1.2<br>0.8<br>1.5 | 0.3<br>0.3<br>0.4<br>0.5 | 0.3<br>0.5<br>0.2<br>0.5 | 0.5<br>0.3<br>0.3<br>0.5 | 2.6<br>1.2<br>0.5<br>1.4 | 0.5<br>0.8<br>0.5<br>0.5 | } BJAB |

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<223> OTHER INFORMATION: Description of Artificial Sequence: Synthetic
      protein-binding motif

<400> SEQUENCE: 1

Pro Xaa Gln Thr Xaa
  1               5

<210> SEQ ID NO 2
<211> LENGTH: 711
<212> TYPE: DNA
<213> ORGANISM: Epstein-Barr virus
<220> FEATURE:
<221> NAME/KEY: CDS
<222> LOCATION: (1)..(711)
```

<400> SEQUENCE: 2

```
cag gtg cag ctg gtg caa tct ggg tct gag ttg aag aag cct ggg tcc    48
Gln Val Gln Leu Val Gln Ser Gly Ser Glu Leu Lys Lys Pro Gly Ser
 1               5                  10                  15 tcg gtg aag gtc tcc tgc aag gct tct gga ggc acc ttc agc agc tat    96
Ser Val Lys Val Ser Cys Lys Ala Ser Gly Gly Thr Phe Ser Ser Tyr
             20                  25                  30 gct atc agc tgg gtg cga cag gcc cct gga caa ggg ctt gag tgg atg   144
Ala Ile Ser Trp Val Arg Gln Ala Pro Gly Gln Gly Leu Glu Trp Met
         35                  40                  45 gga ggg atc atc cct atc ttt ggt aca gca aac tac gca cag aag ttc   192
Gly Gly Ile Ile Pro Ile Phe Gly Thr Ala Asn Tyr Ala Gln Lys Phe
     50                  55                  60 cag ggc aga gtc acg att acc gcg gac aaa tcc acg agc aca gcc tac   240
Gln Gly Arg Val Thr Ile Thr Ala Asp Lys Ser Thr Ser Thr Ala Tyr
 65                  70                  75                  80 atg gag ctg agc agc ctg aga tct gag gac acg gcc gtg tat tac tgt   288
Met Glu Leu Ser Ser Leu Arg Ser Glu Asp Thr Ala Val Tyr Tyr Cys
                 85                  90                  95 gcg aga ggg agg gac ggt atg gac gtc tgg ggt caa ggc acc ctg gtc   336
Ala Arg Gly Arg Asp Gly Met Asp Val Trp Gly Gln Gly Thr Leu Val
            100                 105                 110 acc gtc tcc tca ggt ggc ggc ggt tcc gga ggt ggt ggt tct ggc ggt   384
Thr Val Ser Ser Gly Gly Gly Gly Ser Gly Gly Gly Gly Ser Gly Gly
        115                 120                 125 ggc agc cag cct ggg ctg act cag cca ccc tca gtg tcc gtg tcc       432
Gly Gly Ser Gln Pro Gly Leu Thr Gln Pro Pro Ser Val Ser Val Ser
    130                 135                 140 cca gga cag aca gcc agc atc acc tgc tct gga gat gaa ttg ggg aat   480
Pro Gly Gln Thr Ala Ser Ile Thr Cys Ser Gly Asp Glu Leu Gly Asn
145                 150                 155                 160 aga tat gct tac tgg tat cag cag aag cca ggc cag tcc cct gtt ctg   528
Arg Tyr Ala Tyr Trp Tyr Gln Gln Lys Pro Gly Gln Ser Pro Val Leu
                165                 170                 175 gtc atc tat caa gat agg aag cgg ccc tca ggg atc cct gag cga ttc   576
Val Ile Tyr Gln Asp Arg Lys Arg Pro Ser Gly Ile Pro Glu Arg Phe
            180                 185                 190 tct ggc tcc aac tct ggg aac aca gcc act ctg acc atc agc ggg acc   624
Ser Gly Ser Asn Ser Gly Asn Thr Ala Thr Leu Thr Ile Ser Gly Thr
        195                 200                 205 cag gct atg gat gag gct gac tat tac tgt cag gcg tgg gcc agc ggc   672
Gln Ala Met Asp Glu Ala Asp Tyr Tyr Cys Gln Ala Trp Ala Ser Gly
    210                 215                 220 act gga gtc ttc gga act ggg acc aag gtc acc gtc ctt               711
Thr Gly Val Phe Gly Thr Gly Thr Lys Val Thr Val Leu
225                 230                 235
```

<210> SEQ ID NO 3
<211> LENGTH: 237
<212> TYPE: PRT
<213> ORGANISM: Epstein-Barr virus

<400> SEQUENCE: 3

```
Gln Val Gln Leu Val Gln Ser Gly Ser Glu Leu Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45
```

```
Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Arg Asp Gly Met Asp Val Trp Gly Gln Gly Thr Leu Val
            100                 105                 110

Thr Val Ser Ser Gly Gly Gly Ser Gly Gly Gly Gly Ser Gly Gly
             115                 120                 125

Gly Gly Ser Gln Pro Gly Leu Thr Gln Pro Pro Ser Val Ser Val Ser
 130                 135                 140

Pro Gly Gln Thr Ala Ser Ile Thr Cys Ser Gly Asp Glu Leu Gly Asn
145                 150                 155                 160

Arg Tyr Ala Tyr Trp Tyr Gln Gln Lys Pro Gly Gln Ser Pro Val Leu
                165                 170                 175

Val Ile Tyr Gln Asp Arg Lys Arg Pro Ser Gly Ile Pro Glu Arg Phe
            180                 185                 190

Ser Gly Ser Asn Ser Gly Asn Thr Ala Thr Leu Thr Ile Ser Gly Thr
            195                 200                 205

Gln Ala Met Asp Glu Ala Asp Tyr Tyr Cys Gln Ala Trp Ala Ser Gly
    210                 215                 220

Thr Gly Val Phe Gly Thr Gly Thr Lys Val Thr Val Leu
225                 230                 235
```

<210> SEQ ID NO 4
<211> LENGTH: 705
<212> TYPE: DNA
<213> ORGANISM: Epstein-Barr virus
<220> FEATURE:
<221> NAME/KEY: CDS
<222> LOCATION: (4)..(705)

<400> SEQUENCE: 4

```
tag gtg cag ctg gtg cag tct ggg gct gag gtg aag aag cct ggg tcc      48
    Val Gln Leu Val Gln Ser Gly Ala Glu Val Lys Lys Pro Gly Ser
     1               5                  10                  15 tcg gtg aag gtc tcc tgc aag gct tct ggc gtc acc ttc agc agc tat      96
Ser Val Lys Val Ser Cys Lys Ala Ser Gly Val Thr Phe Ser Ser Tyr
                 20                  25                  30 ggt atc aat tgg gtc cga cag gcc cct gga caa gga ctt gaa tgg atg     144
Gly Ile Asn Trp Val Arg Gln Ala Pro Gly Gln Gly Leu Glu Trp Met
             35                  40                  45 gga gga atc att cct atc ttc ggc aca gga aac tac gca cag aag ttc     192
Gly Gly Ile Ile Pro Ile Phe Gly Thr Gly Asn Tyr Ala Gln Lys Phe
         50                  55                  60 cag ggc cga ctc aca ata agc gcg gac gaa tcc acg agc aca gcc tac     240
Gln Gly Arg Leu Thr Ile Ser Ala Asp Glu Ser Thr Ser Thr Ala Tyr
 65                  70                  75 atg gaa ctg aac agt ctg aga tct gag gac acg gcc gtg tat tac tgt     288
Met Glu Leu Asn Ser Leu Arg Ser Glu Asp Thr Ala Val Tyr Tyr Cys
 80                  85                  90                  95 gcg aga ggc aac ccg ttc ggg caa act tgg ggc cag gga acc ctg gtc     336
Ala Arg Gly Asn Pro Phe Gly Gln Thr Trp Gly Gln Gly Thr Leu Val
                100                 105                 110 acc gtc tcc tca ggt ggc ggc ggt tcc gga ggt ggt ggt tct ggc ggt     384
Thr Val Ser Ser Gly Gly Gly Gly Ser Gly Gly Gly Gly Ser Gly Gly
            115                 120                 125
```

```
ggt ggc agc cag cct ggg ctg act cag cca ccc tca gtg tcc cca gga         432
Gly Gly Ser Gln Pro Gly Leu Thr Gln Pro Pro Ser Val Ser Pro Gly
        130                 135                 140 cag aca gcc agc atc acc tgt tct gga gat aaa ttg ggg gat aaa tat         480
Gln Thr Ala Ser Ile Thr Cys Ser Gly Asp Lys Leu Gly Asp Lys Tyr
145                 150                 155 gct tcc tgg tat cag ctg aag cca ggc cag tcc cct cta ctg gtc atc         528
Ala Ser Trp Tyr Gln Leu Lys Pro Gly Gln Ser Pro Leu Leu Val Ile
160                 165                 170                 175 tat caa gat gtc aag cgg ccc tca ggg atc cct gag cga ttc tct ggc         576
Tyr Gln Asp Val Lys Arg Pro Ser Gly Ile Pro Glu Arg Phe Ser Gly
                180                 185                 190 tcc aac tct ggg aac aca gcc act ctg acc atc agc ggg acc cag gct         624
Ser Asn Ser Gly Asn Thr Ala Thr Leu Thr Ile Ser Gly Thr Gln Ala
            195                 200                 205 atg gat gag gct gac tat tac tgt cag gcg tgg gac agc ggc act gcg         672
Met Asp Glu Ala Asp Tyr Tyr Cys Gln Ala Trp Asp Ser Gly Thr Ala
        210                 215                 220 gtt ttc ggc ggg ggg acc aag ctg acc gtc ctg                             705
Val Phe Gly Gly Gly Thr Lys Leu Thr Val Leu
        225                 230

<210> SEQ ID NO 5
<211> LENGTH: 234
<212> TYPE: PRT
<213> ORGANISM: Epstein-Barr virus

<400> SEQUENCE: 5

Val Gln Leu Val Gln Ser Gly Ala Glu Val Lys Lys Pro Gly Ser Ser
 1               5                  10                  15

Val Lys Val Ser Cys Lys Ala Ser Gly Val Thr Phe Ser Ser Tyr Gly
            20                  25                  30

Ile Asn Trp Val Arg Gln Ala Pro Gly Gln Gly Leu Glu Trp Met Gly
        35                  40                  45

Gly Ile Ile Pro Ile Phe Gly Thr Gly Asn Tyr Ala Gln Lys Phe Gln
    50                  55                  60

Gly Arg Leu Thr Ile Ser Ala Asp Glu Ser Thr Ser Thr Ala Tyr Met
65                  70                  75                  80

Glu Leu Asn Ser Leu Arg Ser Glu Asp Thr Ala Val Tyr Tyr Cys Ala
                85                  90                  95

Arg Gly Asn Pro Phe Gly Gln Thr Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gln Pro Gly Leu Thr Gln Pro Pro Ser Val Ser Pro Gly Gln
    130                 135                 140

Thr Ala Ser Ile Thr Cys Ser Gly Asp Lys Leu Gly Asp Lys Tyr Ala
145                 150                 155                 160

Ser Trp Tyr Gln Leu Lys Pro Gly Gln Ser Pro Leu Leu Val Ile Tyr
                165                 170                 175

Gln Asp Val Lys Arg Pro Ser Gly Ile Pro Glu Arg Phe Ser Gly Ser
            180                 185                 190

Asn Ser Gly Asn Thr Ala Thr Leu Thr Ile Ser Gly Thr Gln Ala Met
        195                 200                 205

Asp Glu Ala Asp Tyr Tyr Cys Gln Ala Trp Asp Ser Gly Thr Ala Val
    210                 215                 220
```

Phe Gly Gly Gly Thr Lys Leu Thr Val Leu
225                 230

<210> SEQ ID NO 6
<211> LENGTH: 714
<212> TYPE: DNA
<213> ORGANISM: Epstein-Barr virus
<220> FEATURE:
<221> NAME/KEY: CDS
<222> LOCATION: (1)..(714)

<400> SEQUENCE: 6

```
cag gtg cag ctg gtg cag tct ggg gct gag gtg aag aag cct ggg tcc      48
Gln Val Gln Leu Val Gln Ser Gly Ala Glu Val Lys Lys Pro Gly Ser
  1               5                  10                  15 tcg gtg aag gtc tcc tgc aag gct tct gga ggc acc ttc agc agc tat      96
Ser Val Lys Val Ser Cys Lys Ala Ser Gly Gly Thr Phe Ser Ser Tyr
             20                  25                  30 gct atc agc tgg gtg cga cag gcc cct gga caa ggg ctt gag tgg atg     144
Ala Ile Ser Trp Val Arg Gln Ala Pro Gly Gln Gly Leu Glu Trp Met
         35                  40                  45 gga ggg atc atc cct atc ttt ggt aca gca aac tac gca cag aag ttc     192
Gly Gly Ile Ile Pro Ile Phe Gly Thr Ala Asn Tyr Ala Gln Lys Phe
     50                  55                  60 cag ggc aga gtc acg att acc gcg gac gaa tcc acg agc aca gcc tac     240
Gln Gly Arg Val Thr Ile Thr Ala Asp Glu Ser Thr Ser Thr Ala Tyr
 65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                 85                  90                  95 gcg agg ccc tat ttg ggc tgg ggc caa ggg aca atg gtc acc gtc tct     336
Ala Arg Pro Tyr Leu Gly Trp Gly Gln Gly Thr Met Val Thr Val Ser
            100                 105                 110 tca ggt ggc ggc ggt tcc gga ggt ggt ggt tct ggc ggt ggc agc          384
Ser Gly Gly Gly Gly Ser Gly Gly Gly Gly Ser Gly Gly Gly Ser
        115                 120                 125 aat ttt atg ctg act cag ccc cac tct gtg tcg gag tct ccg ggg aag     432
Asn Phe Met Leu Thr Gln Pro His Ser Val Ser Glu Ser Pro Gly Lys
    130                 135                 140 acg gta aac atc tcc tgc acc cgc agc agt ggc agc att gcc agc cac     480
Thr Val Asn Ile Ser Cys Thr Arg Ser Ser Gly Ser Ile Ala Ser His
145                 150                 155                 160 tac gtg cag tgg ttc cag cag cgc ccg ggc agt gcc ccc gcc act gtg     528
Tyr Val Gln Trp Phe Gln Gln Arg Pro Gly Ser Ala Pro Ala Thr Val
                165                 170                 175 atc tat gag gat aaa caa aga ccc tct ggg gtc cct gat cgg ttc tct     576
Ile Tyr Glu Asp Lys Gln Arg Pro Ser Gly Val Pro Asp Arg Phe Ser
            180                 185                 190 ggc tcc atc gac agc tcc tcc aac tct gcc tcc ctc acc atc tct gga     624
Gly Ser Ile Asp Ser Ser Ser Asn Ser Ala Ser Leu Thr Ile Ser Gly
        195                 200                 205 ctg agg act gaa gac gag gct gac tac tac tgc cag tct tat gat acc     672
Leu Arg Thr Glu Asp Glu Ala Asp Tyr Tyr Cys Gln Ser Tyr Asp Thr
    210                 215                 220 ggc act tgg gtg ttc ggc gga ggg acc aag ctg act gtc ctg              714
Gly Thr Trp Val Phe Gly Gly Gly Thr Lys Leu Thr Val Leu
225                 230                 235
```

<210> SEQ ID NO 7
<211> LENGTH: 238
<212> TYPE: PRT
<213> ORGANISM: Epstein-Barr virus

```
<400> SEQUENCE: 7

Gln Val Gln Leu Val Gln Ser Gly Ala Glu Val Lys Lys Pro Gly Ser
  1               5                  10                  15

Ser Val Lys Val Ser Cys Lys Ala Ser Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Pro Tyr Leu Gly Trp Gly Gln Gly Thr Met Val Thr Val Ser
            100                 105                 110

Ser Gly Gly Gly Gly Ser Gly Gly Gly Gly Ser Gly Gly Gly Gly Ser
            115                 120                 125

Asn Phe Met Leu Thr Gln Pro His Ser Val Ser Glu Ser Pro Gly Lys
            130                 135                 140

Thr Val Asn Ile Ser Cys Thr Arg Ser Ser Gly Ser Ile Ala Ser His
145                 150                 155                 160

Tyr Val Gln Trp Phe Gln Gln Arg Pro Gly Ser Ala Pro Ala Thr Val
                165                 170                 175

Ile Tyr Glu Asp Lys Gln Arg Pro Ser Gly Val Pro Asp Arg Phe Ser
                180                 185                 190

Gly Ser Ile Asp Ser Ser Ser Asn Ser Ala Ser Leu Thr Ile Ser Gly
                195                 200                 205

Leu Arg Thr Glu Asp Glu Ala Asp Tyr Tyr Cys Gln Ser Tyr Asp Thr
                210                 215                 220

Gly Thr Trp Val Phe Gly Gly Gly Thr Lys Leu Thr Val Leu
225                 230                 235

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      Illustrative motif

<400> SEQUENCE: 8

Lys Asp Glu Leu
  1
```

ANTIBODY TO LATENT MEMBRANE PROTEINS AND USES THEREOF

CROSS-REFERENCE TO RELATED APPLICATIONS

This application is a 371 National Phase Entry Application of co-pending International Application PCT/US02/38849, filed 4 Dec. 2002, which designated the U.S. and which claims the benefit under 35 U.S.C. §119(e) of U.S. Provisional Application 60/337,294, filed 4 Dec. 2001.

FIELD OF THE INVENTION

The present invention relates to antibodies to latent membrane proteins 1 (LMP1) and 2, (LMP2A and LMP2B) and antigenic fragments thereof, and more particularly, the extracellular transmembrane loops of the LMP1 protein. The invention further relates to use of these antibodies in prevention and treatment of diseases caused by Epstein-Barr virus (EBV).

BACKGROUND OF THE INVENTION

Latent membrane protein 1 (LMP1) oncogene belongs to a group of antigens expressed on the surface of cells infected with the Epstein-Barr virus (EBV) during the latency period and is considered to be one of the most important EBV-transforming proteins [Meij et al., J. Infectious Diseases, 179:1108-15, 1999]. LMP1 belongs to a group of EBV antigens. Currently known members of this group of antigens include two EBV encoded noncoding RNAs (EBER1, 2), six Epstein-Barr nuclear antigens (EBNA1, 2, 3a, 3b, LP), and three latent membrane proteins (LMP1, 2A, 2B) [Id.].

LMP1 protein has a short cytoplasmic amino terminus which is involved in transcriptional activation. The carboxy terminus contains a C-terminal activation region 1 (CTAR1) region adjacent to the plasma membrane, including a PXQTX (SEQ ID NO. 1) core TRAF protein-binding motif and an outermost CTAR2 region for tumor necrosis factor associated death domain protein (TRADD) and receptor interacting protein (RIP) binding. In addition to these functional domains, LMP1 also contains three plasma membrane spanning domains, which expose short loops to the extracellular space [Knecht et al. Oncology 60:289-302, 2001]. While these short loops are present on the surface of the infected cell, the LMP1 oncogene is known to have a very low immunogenicity [Meij et al. J. Infectious Diseases, 179:1108-15, 1999]. This has hampered development of antibodies against it. Moreover, the extracellular loops of the LMP1 are part of a transmembrane domain. Membrane association of LMP1 makes production of antibodies against a recombinant antigen difficult because such a recombinant antigens do not present themselves in a native membrane-bound conformation.

Epstein Barr Virus (EBV) belongs to γ-herpesviruses and it is associated with various malignant and benign lymphoproliferative disorders [Liebowitz, N. Eng. J. Med. 338:1413-21 (1998)]. It is the etiologic agent of infectious mononucleosis. It is also strongly associated with malignancies like Burkitt's Lymphoma (BL), nasopharyngeal carcinoma, and immunoblastic B cell lymphomas (non-Hodgkin's lymphoma, NHL) in immunocompromised individuals. EBV has also been detected in substantial percentage of Hodgkin's disease (HD), in certain types of T and NK (natural killer) cell NHL (T-NHL and B-NHL), and gastric carcinoma patients. In addition to its association of human malignancies, EBV is also associated with a spectrum of diseases, collectively called chronic EBV syndrome, and with oral hairy cell leukoplakia predominantly seen in patients with AIDS.

Based upon viral latent gene expression and the expression of surface antigens, three main types of EBV latency have been characterized. In type I latency, the EBV infected cells express EBNA-1 and EBER1 and 2, and the disease is usually a phenotypically representative BL. Type II latency is seen in nasopharyngeal carcinoma, Hodgkin's disease, T-cell non-Hodgkin's lymphoma, and B-cell non-Hodgkin's lymphoma, and in immunocompetent patients and is characterized by expression of EBNA1, EBER1 and EBER2, and LMP1, LMP2A, and LMP2B. Type II latency, in which all gene products are expressed, is seen in B-NHL in immunocompromised patients.

In many cases, EBV infection results in a lymphoproliferative disease that may be only temporarily debilitating. However, in immunosuppressed individuals, the result can be full-blown malignancy. This occurs in individuals who are immunosuppressed intentionally, particularly children receiving organ transplants who are treated with cyclosporine A, or opportunistically, as in the case with individuals infected with EBV, or genetically, as in the case of affected males carrying the XLP (X-linked lymphoproliferative syndrome) gene. In these cases the resulting malignancies derive from the polyclonal proliferation of EBV-infected B cells. In addition, in such patients uncontrolled epithelial replication of the virus is detectable in lesions of oral hairy leukoplakia Thus, the immune response plays a central role in the control of EBV infection.

Vaccination against EBV might be useful for several groups of people who are seronegative for EBV. These include patients undergoing bone marrow or organ transplantation, persons with X-linked lymphoproliferative disease, people in areas of the world with high incidence of Burkitt's lymphoma (equatorial Africa) or nasopharyngeal carcinoma (southern China), and adolescents and adults at risk for infectious mononucleosis.

Current treatment of BL and other EBV associated malignancies include chemotherapy, for example cyclophosphamide, and/or radiation therapy. Radiation therapy is frequently used, especially in patients with AIDS, because chemotherapy alone is rarely successful. However, these treatments are focused on unspecific general destruction of rapidly dividing cells and are associated with a number of undesirable side effects.

Some anti-B-cell antibodies, such as monoclonal antibodies to CD21 (EBV receptor), CD24 (pan-B-cell antibody), and CD20 (Rituxan®, rituximab, from Genetech oncobiology, Inc.) have recently been introduced [Cohen J. I., New England J. Med. 343:481-492, 2000; Benkerrou et al., Blood 92:3137-47 (1998)]. However, while being B-cell specific, they do not discriminate between EBV infected and uninfected B-cells and their use results in destruction of all B-cells with such surface antigens. Therefore it would be desirable to develop antibodies that are specific for EBV infected cells and that elicit sufficient immune responses to specifically target infected with EBV infected cells. It would also be desirable to have new means for determining cells infected by EBV and means which can be used to differentiate between different disease states.

SUMMARY OF THE INVENTION

We have now discovered antibodies and antibody fragments directed against extracellular domains of the EBV LMP proteins, including LMP1, LMP2A and LMP2B. Generating antibodies against LMP1 is preferred. However, the same methodology can be used for all three proteins. We have also discovered methods of treating EBV-associated malignancies using these LMP specific antibodies. For example, these antibodies can further be expressed intracellularly to bind to LMP1 protein within the cell and inhibit function of the protein. We have also discovered methods of generating immune cells, including cytotoxic T cells, with specificity for LMP. We have also discovered methods of treating EBV-associated malignancies using these LMP-specific immune cells. We have further discovered a method of using the antigenic fragments of, e.g., LMP1 in eliciting immune response, for example, in a vaccine formulation.

One embodiment of the invention provides an antibody or antibody fragment that binds to Epstein Barr Virus (EBV) latent membrane protein (LMP). Preferably, the antibody binds to LMP1, LMP2A, or LMP2B. Even more preferably, LMP1. In a preferred embodiment, the antibody binds to an antigenic fragment which is an extracellular domain of the LMP1. In a more preferred embodiment, the antigenic fragment is amino acids 1-207 of LMP1. Preferably, the antibody is a single chain antibody, a single chain Fv domain (scFv, also sometimes called sFv), Fab, Fab', F(ab)$_2$, humanized antibody, human antibody, or chimeric antibody.

Another preferred embodiment of the invention provides an immunogenic proteoliposome containing LMP. Preferably, the proteoliposome contains at least one antigenic epitope of the extracellular domain of LMP1. In a preferred embodiment, the proteoliposome contains the extracellular domain of LMP1, which can readily be prepared for instance using LMP1 amino acids 1-207. Preferably, the proteoliposome contains the entire extracellular domain of the particular LMP being used.

Another preferred embodiment of the invention provides a method of obtaining an LMP-specific antibody, by screening a library of antibodies with a proteoliposome containing LMP, and selecting antibodies that bind to the proteoliposome. Preferably, the library of antibodies is a phage display library. Even more preferably, a human single chain antibody phage display library.

In another embodiment, the invention relates to a pharmaceutical composition comprising a complex comprising the antibody or antibody fragment against an antigenic fragment of LMP, e.g., LMP1 and a second moiety, such as a cytotoxic molecule attached to the antibody in a pharmaceutically acceptable carrier.

In a further embodiment, the invention relates to a method of treating an EBV-associated disease. Preferred EBV-associated diseases include an EBV-associated malignancy, Hodgkin's disease, chronic EBV syndrome, and oral hairy cell leukoplakia. Preferably, an EBV-associated malignancy including Burkitt's lymphoma, lymphoproliferative disease, B-lymphoproliferative disease, non-Hodgkin'lymphoma (NHL), T-NHL, NK-NHL, lymphonasopharyngeal carcinoma, and gastric carcinoma.

One preferred embodiment comprises administering the antibody or antibody fragment against an antigenic fragment of LMP, for example, LMP1 in a pharmaceutically acceptable carrier to an individual infected with EBV. In one embodiment, the individual has EBV-infected cells, more preferably an EBV-associated malignancy. One preferred compound further contains a second moiety such as a cytotoxic molecule attached to the antibody.

In yet another embodiment, the invention relates to a method of vaccinating an individual against EBV infection using an immune response eliciting amount of at least one LMP protein, e.g., LMP1, or an antigenic fragment thereof in a pharmaceutically acceptable carrier.

Another preferred embodiment of the present invention provides a chimeric gene comprising one gene segment encoding at least an antibody heavy chain binding region which specifically binds LMP, (e.g., a dAb, a scFv) and a second gene segment encoding partially or entirely the transmembrane and cytoplasmic domains of an immune cell-triggering molecule. More preferably, the first gene segment encodes both the light and heavy chain binding region, e.g., a single chain antibody. Such a chimeric gene combines the antibody recognition sites and the lymphocyte signaling moiety into one continuous chain, and endows a lymphocyte transformed with this chimeric gene with antibody-type specificity. Preferably, there is both a transmembrane and a cytoplasmic domain, although it is possible to delete the cytoplasmic domain.

In one preferred embodiment, the antibody binding region is an scFv.

In one preferred embodiment, the immune cell-triggering molecule is a lymphocyte receptor chain, a polypeptide of the TCR/CD3 complex, a subunit of the Fc receptor, or a subunit of the IL-2 receptor. Even more preferably, a chain of the T cell receptor. Even more preferably, a cytotoxic T cell receptor.

Another preferred embodiment provides an expression vector containing the chimeric gene combining an LMP-specific antibody heavy chain binding region with an immune cell-triggering molecule.

Another preferred embodiment of the present invention provides LMP-specific immune cells, transformed with the chimeric gene combining an LMP-specific antibody binding region with an immune cell-triggering molecule. Preferrably, the immune cell is a natural killer cell, a lymphokine activated cell, a cytotoxic T cell, a helper T cell, or a subtype thereof. Even more preferably, a cytotoxic T cell.

Another preferred embodiment of the present invention provides methods of treating an EBV-associated disease by administering an immune cell expressing a chimeric gene combining an LMP-specific scFv with an immune cell-triggering molecule. Preferably, an EBV-associated malignancy. Preferably, the immune cell expressing a chimeric gene is a cytotoxic T cell. Preferably, the binding of the immune cells to the LMP-expressing target cells results in cell death of the target cells.

In another preferred embodiment of the present invention, the chimeric gene combining an LMP-specific antibody heavy chain binding region with an immune cell-triggering molecule is transformed into the lymphocytes of an individual infected with EBV, and the transformed and thus activated cells are administered to the individual.

[$^{35}$S]cysteine labeled cells were used to obtain proteoliposomes. The proteoliposomes were incubated in SDS-sample buffer and the eluted proteins analysed in a SDS-PAGE gel. The position of ΔTES-C9 (24 KDa) is indicated.

Figure 1:
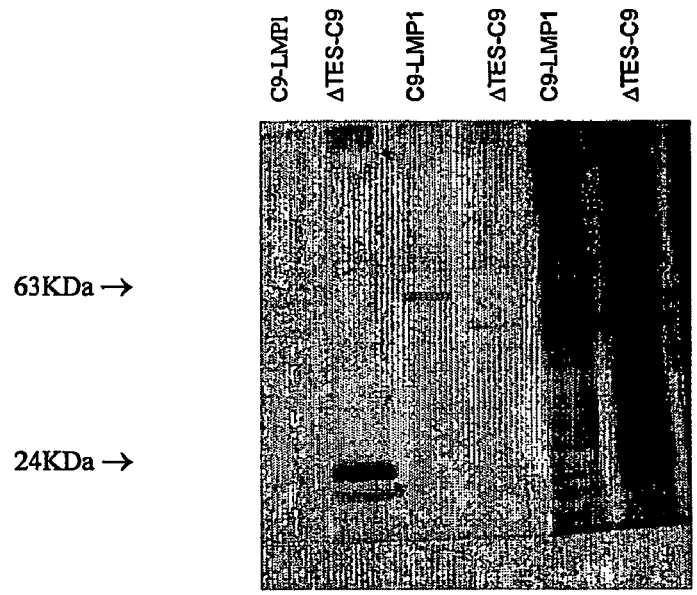
FIG. 1 shows expression of C9-LMP1 and ΔTES-C9 in COS-7, 293 and CF2 cells. Cell lysates derived from approximately $10^7$ COS-7 or 293 or CF2 cells transfected with pC9-LMP1 or pΔTES-C9 were subjected to immunoprecipitation with anti-C9 Sepharose beads. Bound proteins were recovered by incubation in 2% SDS buffer at 55° C. Eluted proteins were separated on a 12% or 15% SDS-PAGE mini-gel.
Figure 2:
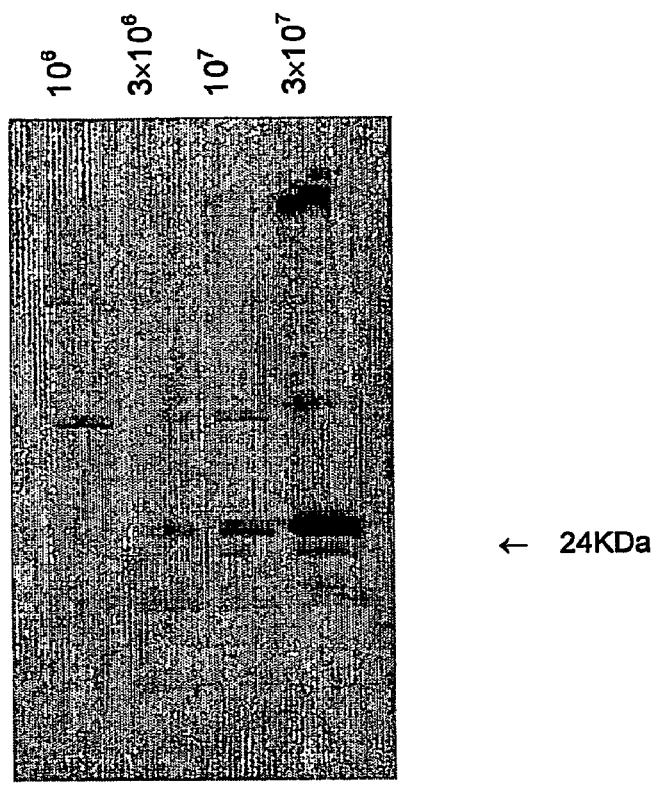
FIG. 2 shows an SDS-PAGE gel analysis of different cell/bead ratios. Radiolabeled cleared lysates derived from approximately $10^7$ COS-7 cells incubated respectively with $10^6$, $3 \times 10^6$, $10^7$, $3 \times 10^7$ 1D4-streptavidin-coated beads. Beads were washed several times and the proteins eluted by incubation at 55° C. for 1 h.
Figure 3:
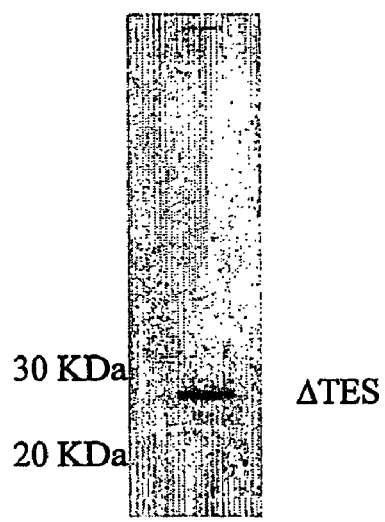
FIG. 3 shows an SDS-PAGE gel analysis of protein composition of ΔTES-C9 proteoliposomes. [$^{35}$S]methionine.
Figure 4B:
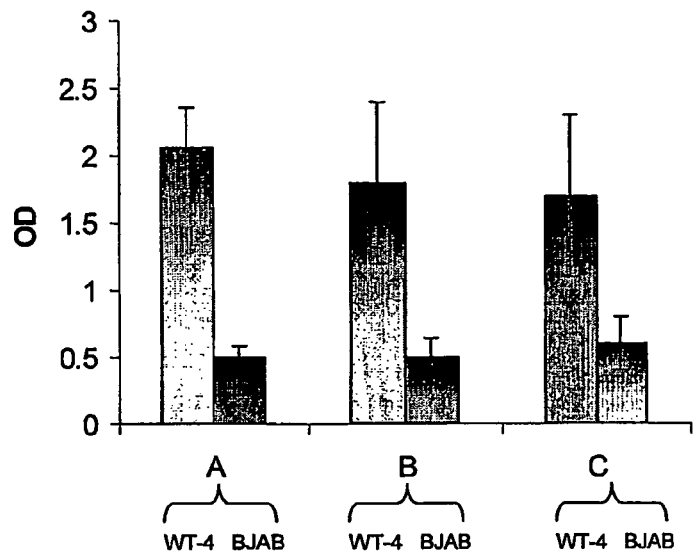

FIGS. 4A and B show the results of an ELISA assay after panning of a phage library with ΔTES-C9 proteoliposomes. The ΔTES-C9 proteoliposomes were used to select recombinant antibodies from a human single-chain antibody phage display library of approximately $1.5 \times 10^{10}$ members. Each round of selection was performed using approximately $5 \times 10^7$ proteoliposomes; in the first round $2 \times 10^{13}$ t.u. of phages were used and the output was 105 t.u./ml. After the fourth round the output was $5 \times 10^7$ t.u./ml. After the fourth round of panning, 48 of the selected individual phages were tested for ability to bind BJAB-WT4 cells relative to binding of BJAB cells using a cell-based ELISA. The titer of the captured phages increased from $10^5$ to $5 \times 10^7$ from the second to the fourth round of panning. All resulted positive in the cell-based ELISA assay as shown in the table on FIG. 4A. FIG. 4B illustrates the ELISA assay using pools A (including clones 1-5, 7-22, 24-26, 28-30, 32-34, 36, 3846, and 48), B (including clones 6, 23, 31, and 35), and C (including clones 37 and 47).

DETAILED DESCRIPTION OF THE INVENTION

The present invention is directed to antibodies and antibody fragments directed against extracellular domains of the EBV LMP proteins, including LMP1, LMP2A and LMP2B. Generating antibodies against LMP1 is preferred. However, the same methodology can be used for all three proteins. We have also discovered methods of treating EBV-associated malignancies using these LMP specific antibodies. For example, these antibodies can further be expressed intracellularly to bind to LMP1 protein within the cell and inhibit function of the protein. We have also discovered methods of generating immune cells, including cytotoxic T cells, with specificity for LMP. We have also discovered methods of treating EBV-associated malignancies using these LMP-specific immune cells. We have further discovered a method of using the antigenic fragments of, e.g., LMP1 in eliciting immune response, for example, in a vaccine formulation.

The antibodies and antibody fragments of the present invention recognize the extracellular epitope of an LMP. Preferably, the LMP is LMP1, LMP2A, or LMP2B. Even more preferably, LMP1.

Antibodies and antibody fragments of the present invention include single chain antibodies, single chain Fv domains (scFv, also sometimes called sFv), Fab, Fab', F(ab)$_2$, heavy chain single domain (dAb), humanized antibodies, human antibodies, and chimeric antibodies. One preferred antibody is an scFv antibody. Even more preferably, a human scFv.

Any antigen or antigenic determinant which can generate LMP-specific antibodies may be used to generate such antibodies. Preferred antigens include proteoliposomes containing LMP, as described below.

Preferably, the antigenic determinant has a conformation approximating the wild type (i.e., native) LMP such as LMP1. The invention is further directed to antibodies or fragments thereof capable of specifically recognizing an epitope of an LMP, such as the LMP1 protein or derivatives thereof and capable of binding thereto.

In one preferred embodiment, the antigenic determinant is part of an extracellular loop of LMP1. For example, the antigenic determinant can be made from about amino acids 1-207 of LMP1. This construct contains the cytoplasmic N-terminus, the six transmembrane domains and 20 amino acids of the C-terminal tail. Obviously, other variations can be made. For example, the C-terminal tail can be modified as can the other positions. Preferably, modifications are designed to emphasize the native antigenic epitopes. More preferably, a conserved epitope among EBV strains.

The LMP antigens useful according to the present invention include latent membrane protein 1 (LMP1), LMP2A, and LMP2B and antigenic fragments thereof. In the preferred embodiment, the antigen is LMP1. Preferably, the antigen comprises at least one of the extracellular loops of LMP1. One preferred method of generating an antibody is to prepare proteoliposomes which contain an antigenic determinant of an LMP protein such as LMP1. The epitope is preferably in a conformation that approximates the wild type conformation. This can be done by known means based upon this disclosure. The basic methodology described below can be used with all the LMPs.

One source of antigenic material to generate antibodies is proteoliposomes containing LMP. One method for expressing proteins including transmembrane proteins such as LMPs is the use of proteoliposomes, as described in PCT/US01/50820, PCT/US00/35295, and U.S. Ser. No. 09/749,240, which are hereby incorporated by reference.

To prepare proteoliposomes containing LMP, a vector expressing the desired portion of LMP is expressed into a host cell, as described below. The LMP-expressing cell is then lysed in a buffer with the appropriate detergent and protease inhibitors so the LMP can be separated from other cellular debris by conventional means without harming the protein, preferably without disrupting the protein's natural conformation.

In general, due to their amphipathic properties, transmembrane proteins can be solubilized only by agents that disrupt hydrophobic associations and destroy the membrane's lipid bilayer. The agents typically used are small amphipathic molecules which tend to form micelles in water. Preferably, the agent is a detergent. When mixed with membranes, the hydrophobic regions of the detergent bind to the transmembrane domain of proteins, displacing the lipid molecules. The polar ends of detergents can either be charged (ionic) or uncharged (non-ionic). Although integral membrane proteins can be maintained in a native conformation in a detergent solution, over time many such solubilized proteins undergo denaturation and aggregation.

When a detergent is removed from a transmembrane protein-detergent complex in the absence of phospholipid, the membrane protein molecules usually denature, aggregate and precipitate out of solution. If, however, the purified protein is mixed with phospholipid before the detergent is removed, the active protein can insert into the lipid bilayer formed by the phospholipids. In this manner, functionally active membrane proteins can be reconstituted from purified components. An integral membrane protein properly reconstituted into its native lipid environment is stable for extended periods of time.

Additionally, a critical factor for maintaining a functional native conformation of the LMP transmembrane protein during its purification is the choice of detergent used to solubilize the protein. The detergent best suited for a given membrane protein is typically determined empirically. If the protein has been investigated previously, the literature will indicate successful detergents. Moreover, one can rely upon the results obtained with related proteins to determine detergents that will be successful with other proteins. Thus, research on a related protein indicates the type of detergent most likely to extract the protein in an active form.

Detergents can be generally classed, depending upon the nature of their polar end, into three groups: non-ionic, zwitterionic, and ionic. Strong ionic detergents (such as SDS) can solubilize most membrane proteins, but tend to unfold the protein in the process, making them less useful for reconstituting active conformations. In general, milder non-ionic detergents are preferred.

Detergents recommended for gentle solubilization of membrane proteins include alkyl glucopyranosides (such as C8-GP and C9-GP), alkyl thio-glucopyranosides (such as C8-tGP, C10-M, C12-M, Cymal-5, Cymal-6, and Cymal-7), alkyl sucroses (such as HECAMEG), CHAPSO, digitonin, hydroxyethylglucamides (such as HEGA-10), oligoethyleneglycol derivatives (such as C8E5, C8En, and C12E8), dodecylmaltopyranoside, and phenyl polyoxyethylenes (such as Triton X-100).

Preferred detergents include alkyl thioglucopyranosides, dodecylmaltopypanoside and phenyl polyoxyethydenes. More preferably, Cymal-5, Cymal-6, Cymal-7, HEGA-10, digitonin, CHAPSO, dodecylmaltopyranoside, and Triton X-100. Still more preferably Cymal-5, Cymal-6, Cymal-7, and dodecylmaltopyranoside.

Commercial kits are also available to assist in choosing a detergent appropriate for a given membrane protein. For example, both Anatrace and Calbiochem offer a variety of kits containing mixtures of different detergents.

There are many known instances of detergents which have been successfully used to purify functionally active membrane proteins. For example, decylmaltoside was used to purify the $K^+$ channel (Ksc $K^+$) from *Streptomyces lividans*, allowing its structure to be determined by X-ray crystallography (Doyle et al., *Science* (1998) 280: 69-77). Cymal-5, Cymal-6, Cymal-7, and dodecylmaltopypanoside are preferred detergents for GCPRs, more preferably for chemokine receptors (Mirzabekov, T. et al. (1999), *J. Biol. Chem.* 274: 28745-50).

The cleared cell lysate containing all solubilized LMP membrane proteins and other water-soluble cellular proteins can be separated from the other cellular debris by conventional means. For example using high speed centrifugation, such as 150,000×g. Antibodies directed against the epitope tag on the protein of interest are used to capture this protein from the cell lysate onto the solid support (e.g., beads). After binding of the solubilized integral membrane protein to the antibodies immobilized on the solid support, the solid support is washed. Thereafter the purified detergent-protein mixture is formed into a proteoliposome as described below.

The proteoliposome comprises a spherical or elliptoid shape such as a bead or other pellet. Preferably, the bead or pellet is at least about 15% the size of a eukaryotic cell; still more preferably it is at least about 20% the size of such a cell; and even more preferably it is at least about 25% the size of such a cell. The shape is three-dimensional so that it can be coated on all sides. However, there can be substantial variability in the exact shape used. The exact shape chosen will depend upon the way the proteoliposome is being used. Thus, in some embodiments flakes are preferable to beads, e.g., as an immunogen, in others, a thicker ellipsoid can be preferable.

The spherical or elliptoid shape, e.g. bead, is preferably also coated with a substance that will help attract and anchor a lipid layer. For example, one can use a compound such as streptavidin or avidin to coat the spherical or elliptoid shape such as a bead and add a small amount of biotinylated lipid to the lipid mixture. For example, one can use a head group-modified synthetic lipid, such as dipabmitoylphosphoethanolamine-N-Biotinyl (Biotinyl-DPPE) or dioleoylphosphoethanolamine-lissamine Rhodamine B (Rho-DOPE) in solution with lipids. Such a mixture will form a strong uniform coating with, for example, a streptavidin coated-bead.

The spherical or elliptoid shape (such as a bead) will also have an anchor ligand such as an antibody bound to it that will specifically bind either the antigenic tag or a known specific portion of the integral membrane protein that is to be bound to the bead, thereby orienting the protein. The lipid solution containing biotinylated lipid is added to the beads with the captured protein of interest. Thereafter, the detergent is slowly removed by known means. For example, by dialysis, for e.g., at least 24 hours. The resulting integral membrane protein-containing proteoliposome is stable for an extended period of time. As used herein, an extended period of time means at least 12 hours; still more preferably at least one day; even more preferably at least one week; still more preferably at least one month; and even more preferably at least two months. Not only will the protein retain its conformation in these proteoliposomes for long periods of time, but it will do so under a wide range of conditions, such as pH and temperature.

Preferably the spherical or elliptoid surface that is used is a magnetic bead. Magnetic beads are well known in the art and can be obtained commercially. For example tosylactivated Dynabeads® M-(Bikker, J. A., Trumpp-Kallmeyer, S., and Humblet, C. (1998) J. Med. Chem. 41, 2911-2927)0 (Dynal, Inc., Lake Success, N.Y.). These are particularly useful in assisting in the purification of the protein. One can use such proteoliposomes as intermediates and transfer the stabilized proteoliposome to another surface. For example, a flake. When using the proteoliposome for injection into an individual, it is preferable that the surface is made of a biodegradable material.

While the proteoliposome will typically contain only the integral membrane protein of interest, there are instances where one may want to use more than one protein. For example, one can prepare a mixture comprising different epitopes of LMP1, LMP2A, or LMP2B, or, alternatively, use LMP2A and LMP2B antigenic fragments together with LMP1 antigenic fragment, or, for example, other EBV viral proteins. This can readily be done by tagging the proteins with the same epitope tag at the C-terminus and preparing beads with the appropriate tag-reactive antibody. Alternatively, the proteins can be tagged with different tags and one can prepare beads having mixtures of different antibodies. This would allow one to vary the ratios of the proteins in the proteoliposome.

These stabilized proteoliposomes can be used in a variety of different methods. One can obtain high concentrations of the protein on the bead. In this manner one can use the proteoliposome as an immunogen to obtain antibodies to the native conformation of the protein. One can use the proteoliposomes to obtain antibodies to different epitopes exposed during different conformations of a protein. For example, one protein may assemble into several different multimeric complexes, depending for example on the availability of different binding partners. Proteoliposomes carrying different complexes can be used as immunogens, thus generating antibodies to different epitopes on a single protein which are differentially exposed depending on its binding to other proteins.

The immunogenic LMP proteoliposomes can be used to generate and also to identify a range of antibodies. For example, LMP1 antibodies.

The immunogenic LMP proteoliposomes can be used to generate an immune reaction in a host by standard means. For example one can administer the LMP1 proteoliposome in adjuvant. Alternatively, the LMP proteoliposome can be used to select antibodies from an antibody library. For example, one can pan a human single chain antibody phage display library.

The LMP proteoliposome is preferably administered with an adjuvant. Adjuvants are well known in the art and include aluminum hydroxide, Ribi adjuvant, etc. Preferably the proteoliposome is comprised of biodegradable material.

One can administer the proteoliposomes to individuals by a variety of means. For immunization purposes, intradermal, subcutaneous, intramuscular and mucosal administration can be used.

The proteoliposomes when used for administration are prepared under aseptic conditions with a pharmaceutically acceptable carrier or diluent.

For preparation of LMP antibodies, any technique that provides for the production of antibody molecules may be used. As stated, preferably the antigen is present as part of a proteoliposome. However, the present invention is not so limited. The term "antibodies" is meant to include monoclonal antibodies, polyclonal antibodies and antibodies prepared by recombinant nucleic acid techniques that are selectively reactive with a desired antigen, such as LMP1 protein or an antigenic epitope thereof.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, single domain heavy chain and others which retain the antigen binding function of the antibody. Monoclonal antibodies of any mammalian species can be used in this invention. In practice, however, the antibodies will typically be humanized or of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The term "selectively reactive" refers to those antibodies that react with one or more antigenic determinants of the desired antigen, e.g., EBV LMP1 protein, and do not react appreciably with other polypeptides. For example, in a competitive binding assay, preferably less than 5% of the antibody would bind another protein, more preferably less than 3%, still more preferably less than 2% and most preferably less than 1%. Antigenic determinants usually consist of chemically active surface groupings of molecules such as amino acids or sugar side chains and have specific three dimensional structural characteristics as well as specific charge characteristics. Antibodies can be used for diagnostic applications or for research purposes.

One method for preparing antibodies is by using hybridoma mRNA or splenic mRNA as a template for PCT amplification of such genes [Huse, et al., *Science* 246:1276 (1989)]. For example, intrabodies can be derived from murine monoclonal hybridomas [Richardson, J. H., et al., *Biochem and Biophys Res Comm.* 197: 422-427 (1993); Mhashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines [Marasco, W. A., et al., *Proc. Natl. Acad. Sci. USA* 90:7889-7893 (1993); Chen, S. Y., et al., *Proc. Natl. Acad. Sci. USA* 91:5932-5936 (1994)].

One preferred method includes the use of an antibody library such as an antibody phage display technology to construct new antibodies against different epitopes on a target molecule [Burton, D. R., et al., *Proc. Natl. Acad. Sci. USA* 88:10134-1-137 (1991); Hoogenboom, H. R., et al., *Immunol. Rev.* 130:41-68 (1992); Winter, G., et al., *Ann Rec. Immunol.* 12:433-355 (1994); Marks, J. D., et al., *J. Biol. Chem.* 267:16007-16010 (1992); Nissim, A., et al., *EMBO J.* 13:692-698 (1994); Vaughan, T. J., et al., *Nature Bio.* 14:309-314 (1996); Marks, C., et al., *New Eng. J. Med.* 335: 730-733 (1996)]. For example, very large naïve human scFv libraries have been and can be created to offer a large source of rearranged antibody genes against a plethora of target molecules. Smaller libraries can be constructed from individuals with autoimmune disorders [Portolano, S, et al., *J. Immunol.* 151: 2839-2851 (1993); Barbas, S. M., et al., *Proc. Natl. Acad. Sci. USA* 92:2529-2533 (1995)] or infectious diseases [Barbas, C. F., et al., *Proc. Natl. Acad. Sci. USA* 89:9339-9343 (1992); Zebedee, S. L., et al., *Proc. Natl. Acad. Sci. USA* 89:3175-3179 (1992)] in order to isolate disease specific antibodies. One can then screen such libraries to select the appropriate antibodies.

Other sources include transgenic mice that contain a human immunoglobulin locus instead of the corresponding mouse locus as well as stable hybridomas that secrete human antigen-specific antibodies [Lonberg, N., et al., *Nature* 368: 856-859 (1994); Green, L. L., et al., *Nat. Genet.* 7:13-21 (1994)]. Such transgenic animals provide another source of human antibody genes through either conventional hybridoma technology or in combination with phage display technology. In vitro procedures to manipulate the affinity and find specificity of the antigen binding site have been reported including repertoire cloning [Clackson, T., et al., *Nature* 352: 624-628); marks, J. D., et al., *J. Mol. Biol.* 222: 581-597 (1991); Griffiths, A. D., et al., *EMBO J.* 12: 725-734 (1993)], in vitro affinity maturation [Marks, J. D., et al., *Biotech* 10: 779-783 (1992); Gram, H., et al., *Proc. Natl. Acad. Sci. USA* 89: 3576-3580 (1992)], semi-synthetic libraries [Hoogenboom, H. R., supra; Barbas, C. F., supra; Akamatsu, Y., et al., *J. Immunol.* 151: 4631-4659 (1993)] and guided selection [Jespers, L. S. et al., *Bio Tech* 12: 899-902 (1994)]. Starting materials for these recombinant DNA based strategies include RNA from mouse spleens [Clackson, t., supra] and human peripheral blood lymphocytes [Portolano, S., et al., supra; Barbas, C. F., et al., supra; Marks, J. D., et al., supra; Barbas, C. F., et al., *Proc. Natl. Acad. Sci. USA* 88: 7978-7982 (1991)].

For preparation of monoclonal antibodies directed toward an antigen, such as the immunogenic proteoliposomes, any technique that provides for the production of antibody molecules by continuous cell lines may be used. For example, the hybridoma technique originally developed by Kohler and Milstein (*Nature*, 256: 495-7, 1973), as well as the trioma technique, the human B-cell hybridoma technique (Kozbor et al., *Immunology Today* 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al., U.S. Pat. Nos. 4,704,694 and 4,976,778).

The monoclonal antibodies may be human monoclonal antibodies or chimeric human-mouse (or other species) monoclonal antibodies. The present invention provides for antibody molecules as well as fragments of such antibody molecules.

Those of ordinary skill in the art will recognize that a large variety of possible moieties can be coupled to the resultant antibodies or preferably to the stabilized trimers or to other molecules of the invention. See, for example, "Conjugate Vaccines", *Contributions to Microbiology and Immunology*, J. M. Cruse and R. E. Lewis, Jr (eds.), Carger Press, New York, 1989, the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents (see Killen and Lindstrom, *J. Immunol.* 133:1335-2549, 1984; Jansen, F. K., et al., *Imm. Rev.* 62:185-216, 1982; and Vitetta et al., supra).

Preferred linkers are described in the literature. See, for example, Ramakrishnan, S., et al., *Cancer Res.* 44: 201-208 (1984), describing the use of MBS (M-maleimidobenzoyl-N-hydroxysuccinimide ester). See also Umemoto et al., U.S. Pat. No. 5,030,719, describing the use of a halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Complexes that form with molecules of the present invention can be detected by appropriate assays, such as the direct binding assay discussed earlier and by other conventional types of immunoassays. In this manner one can screen cells to determine if they are expressing an LMP. Finally elevated levels of, for example, LMP1 can be used diagnostically to confirm a malignancy and prognostically to determine a particular disease stage.

In a preferred embodiment, one could screen a phage display library looking to find antibodies to a given protein or find ligands that will bind to the protein.

One can also use the antibody tag to reverse-orient the proteoliposome. As used herein a reverse-oriented protein will have the portion of the protein that is normally present intracellularly present on the surface of the proteoliposome. Then one can screen for compounds or proteins that affect intracellular interactions. For example, one can look at the binding of intracellular as well as extracellular ligands, as well as compounds or proteins that will affect intracellular as well as extracellular binding.

One can also use this method to identify small antagonists in an assay that looks at compounds that affect binding to LMP.

Accordingly, the LMP proteoliposomes provide an easily manipulable spherical lipid bilayer containing a relatively large amount of pure, oriented and stable LMP membrane protein.

The proteoliposomes are stable for extended periods of time. The integrity of the conformational dependent epitope on the proteins, such as the LMP proteins, is maintained for extended periods of time permitting the uses described above.

Antibodies can be obtained by screening an antibody library, such as a human antibody phage display library. Numerous antibodies can be detected comprising at least 6 different groups. Tables 1-3 show the structure of three exemplary unique scFvs antibodies of the present invention (SEQ ID NOS: 2-7, respectfully).

TABLE 1

| | | | | | | | | | | | | | | | |
|---|---|---|---|---|---|---|---|---|---|---|---|---|---|---|---|
| ←-------------------------------- FR1 --------------------------------→ | | | | | | | | | | | | | | | |
| CAG | GTG | CAG | CTG | GTG | CAA | TCT | GGG | TCT | GAG | TTG | AAG | AAG | CCT | GGG | TCC | TCG | GTG |
| Q | V | Q | L | V | Q | S | G | S | E | L | K | K | P | G | S | S | V |
| ←----------------- FR1 -----------------→ | | | | | | | | | | ←--------- CDR1 ---------→ | | | | | |
| AAG | GTC | TCC | TGC | AAG | GCT | TCT | GGA | GGC | AAC | TTC | AGC | AGC | TAT | GCT | ATC | AGC | TGG |
| K | V | S | C | K | A | S | G | G | T | F | S | S | Y | A | I | S | W |
| ←------------------- FR2 -------------------→ | | | | | | | | | ←---------------- | | | | | | |
| GTG | CGA | CAG | GCC | CCT | GGA | CAA | GGG | CTT | GAG | TGG | ATG | GGA | GGG | ATC | ATC | CCT | ATC |
| V | R | Q | A | P | G | Q | G | L | E | W | M | G | G | I | I | P | I |
| ---------- CRD2 ----------→ | | | | | | | | | ←---------------- | | | | | | | |
| TTT | GGT | ACA | GCA | AAC | TAC | GCA | CAG | AAG | TTC | CAG | GGC | AGA | GTC | ACG | ATT | ACC | GCG |
| F | G | T | A | N | Y | A | Q | K | F | Q | G | R | V | T | I | T | A |
| ←------------------------------ FR3 ------------------------------ | | | | | | | | | | | | | | | |
| GAC | AAA | TCC | ACG | AGC | ACA | GCC | TAC | ATG | GAG | CTG | AGC | AGC | CTG | AGA | TCT | GAG | GAC |
| D | K | S | T | S | T | A | Y | M | E | L | S | S | L | R | S | E | D |
| -----------------→ ←---------- CDR3 ----------→ ←-------------- | | | | | | | | | | | | | | | |
| ACG | GCC | GTG | TAT | TAC | TGT | GCG | AGA | GGG | AGG | GAC | GGT | ATG | GAC | GTC | TGG | GGT | CAA |
| T | A | V | Y | Y | C | A | R | G | R | D | G | M | D | V | W | G | Q |
| ----------- FR4 -----------→ ←------------- Interchain linker ------------- | | | | | | | | | | | | | | |
| GGC | ACC | CTG | GTC | ACC | GTC | TCC | TCA | GGT | GGC | GGC | GGT | TCC | GGA | GGT | GGT | GGT | TCT |
| G | T | L | V | T | V | S | S | G | G | G | G | S | G | G | G | G | S |
| ---------------------→ ←----- VL -----→ ←-------------- FR1 -------------- | | | | | | | | | | | | | | |
| GGC | GGT | GGT | GGC | AGC | CAG | CCT | GGG | CTG | ACT | CAG | CCA | CCC | TCA | GTG | TCC | GTG | TCC |
| G | G | G | G | S | Q | P | G | L | T | Q | P | P | S | V | S | V | S |
| ---------------------→ ←-------------- CDR1 -------------→ | | | | | | | | | | | | | | | |
| CCA | GGA | CAG | ACA | GCC | AGC | ATC | ACC | TGC | TCT | GGA | GAT | GAA | TTG | GGG | AAT | AGA | TAT |
| P | G | Q | T | A | S | I | T | C | S | G | D | E | L | G | N | R | Y |
| ---→ ←------------------------ FR2 ------------------------→ | | | | | | | | | | | | | | | |
| GCT | TAC | TGG | TAT | CAG | CAG | AAG | CCA | GGC | CAG | TCC | CCT | GTT | CTG | GTC | ATC | TAT | CAA |
| A | Y | W | Y | Q | Q | K | P | G | Q | S | P | V | L | V | I | Y | Q |
| ---------- CDR2 ----------→ ←------------------------ FR3 ------------------------ | | | | | | | | | | | | | | | |
| GAT | AGG | AAG | CGG | CCC | TCA | GGG | ATC | CCT | GAG | CGA | TTC | TCT | GGC | TCC | AAC | TCT | GGG |
| D | R | K | R | P | S | G | I | P | E | R | F | S | G | S | N | S | G |
| ------------------------------------------------------------→ | | | | | | | | | | | | | | | |
| AAC | ACA | GCC | ACT | CTG | ACC | ATC | AGC | GGG | ACC | ACG | GCT | ATG | GAT | GAG | GCT | GAC | TAT |
| N | T | A | T | L | T | I | S | G | T | Q | A | M | D | E | A | D | Y |
| ---→ ←-------------- CDR3 --------------→ ←-------------- FR4 -------------- | | | | | | | | | | | | | | |
| TAC | TGT | CAG | GCG | TGG | GCC | AGC | GGC | ACT | GGA | GTC | TTC | GGA | ACT | GGG | ACC | AAG | GTC |
| Y | C | Q | A | W | A | S | G | T | G | V | F | G | T | G | T | K | L |
| ACC | GTC | CTT | | | | | | | | | | | | | | | |
| T | V | L | | | | | | | | | | | | | | | |

FG-1

VH Germline     DP-88/hv1051K

VH Family       VH1

CDR3 length     7

VL Germline     3r.9C5/DPL23

VL Family       VL3

CDR3 length     9

TABLE 2

| ←―――――――――――――――――― FR1 ――――――――――――――――――→ | | | | | | | | | | | | | | |
|---|---|---|---|---|---|---|---|---|---|---|---|---|---|---|
| TAG | GTG | CAG | CTG | GTG | CAG | TCT | GGG | GCT | GAG | GTG | AAG | AAG | CCT | GGG | TCC | TCG | GTG |
| * | V | Q | L | V | Q | S | G | A | E | V | K | K | P | G | S | S | V |

| ←―――――――――― FR1 ――――――――――――→ | | | | | | | ←――――― CDR1 ―――――→ | ←― |
|---|---|---|---|---|---|---|---|---|---|---|---|---|---|---|
| AAG | GTC | TCC | TGC | AAG | GCT | TCT | GGC | GTC | ACC | TTC | AGC | AGC | TAT | GGT | ATC | AAT | TGG |
| K | V | S | C | K | A | S | G | V | T | F | S | S | Y | G | I | N | W |

| ←――――――――――― FR2 ―――――――――――――→ | | | | | | | ←――――――――――― |
|---|---|---|---|---|---|---|---|---|---|---|---|---|---|---|
| GTC | CGA | CAG | GCC | CCT | GGA | CAA | GGA | CTT | GAA | TGG | ATG | GGA | GGA | ATC | ATT | CCT | ATC |
| V | R | Q | A | P | G | Q | G | L | E | W | M | G | G | I | I | P | I |

| ―――――― CRD2 ――――――→ | | | | | | | ←――――――――――――― |
|---|---|---|---|---|---|---|---|---|---|---|---|---|---|---|
| TTC | GGC | ACA | GGA | AAC | TAC | GCA | CAG | AAG | TTC | CAG | GGC | CGA | CTC | ACA | ATA | AGC | GCG |
| F | G | T | G | N | Y | A | Q | K | F | Q | G | R | L | T | I | S | A |

| ←―――――――――――――――――― FR3 ――――――――――――――――――→ | | | | | | | | | | | | | | |
|---|---|---|---|---|---|---|---|---|---|---|---|---|---|---|
| GAC | GAA | TCC | ACG | AGC | ACA | GCC | TAC | ATG | GAA | CTG | AAC | AGT | CTG | AGA | TCT | GAG | GAC |
| D | E | S | T | S | T | A | Y | M | E | L | N | S | L | R | S | E | D |

| ――――――――――――→ | ←――――― CDR3 ―――――→ | ←――――― |
|---|---|---|---|---|---|---|---|---|---|---|---|---|---|---|
| ACG | GCC | GTG | TAT | TAC | TGT | GCG | AGA | GGC | AAC | CCG | TTC | GGG | CAA | ACT | TGG | GGC | CAG |
| T | A | V | Y | Y | C | A | R | G | N | P | F | G | Q | T | W | G | Q |

| ―――――― FR4 ――――――→ | ←――――― Interchain linker ―――――→ | |
|---|---|---|---|---|---|---|---|---|---|---|---|---|---|---|
| GGA | ACC | CTG | GTC | ACC | GTC | TCC | TCA | GGT | GGC | GGC | GGT | TCC | GGA | GGT | GGT | GGT | TCT |
| G | T | L | V | T | V | S | S | G | G | G | G | S | G | G | G | G | S |

| ←――― VL ――――→ | ←――――― FR1 ――――――→ | | | | | | | | | | | | |
|---|---|---|---|---|---|---|---|---|---|---|---|---|---|---|
| GGC | GGT | GGT | GGC | AGC | CAG | CCT | GGG | CTG | ACT | CAG | CCA | CCC | TCA | GTG | TCC | CCA | GGA |
| G | G | G | G | S | Q | P | G | L | T | Q | P | P | S | V | S | P | G |

| ―――――――――――→ | ←―――――――――――― CDR1 ――――――――――――→ | |
|---|---|---|---|---|---|---|---|---|---|---|---|---|---|---|
| GGC | GGT | GGT | GGC | AGC | CAG | CCT | GGG | CTG | ACT | CAG | CCA | CCC | TCA | GTG | TCC | CCA | GGA |
| Q | T | A | S | I | T | C | S | G | D | K | L | G | D | K | Y | A | S |

| ←―――――――― FR2 ―――――――→ | ←――CDR2―――― |
|---|---|---|---|---|---|---|---|---|---|---|---|---|---|---|
| TGG | TAT | CAG | CTG | AAG | CCA | GGC | CAG | TCC | CCT | CTA | CTG | GTC | ATC | TAT | CAA | GAT | GTC |
| W | Y | Q | L | K | P | G | Q | S | P | L | L | V | I | Y | Q | D | V |

| ―――――――→ | ←――――――――――――― FR3 ―――――――――――――→ | |
|---|---|---|---|---|---|---|---|---|---|---|---|---|---|---|
| AAG | CGG | CCC | TCA | GGG | ATC | CCT | GAG | CGA | TTC | TCT | GGC | TCC | AAC | TCT | GGG | AAC | ACA |
| K | R | P | S | G | I | P | E | R | F | S | G | S | N | S | G | N | T |

| ―――――――――――――――――――――――――――→ | | | | | | | | | | | | | | |
|---|---|---|---|---|---|---|---|---|---|---|---|---|---|---|
| GCC | ACT | CTG | ACC | ATC | AGC | CGG | ACC | CAG | GCT | ATG | GAT | GAG | GCT | GAC | TAT | TAC | TGT |
| A | T | L | T | I | S | G | T | Q | A | M | D | E | A | D | Y | Y | C |

| ←――――― CDR3 ―――――→ | ←――――――――― FR4 ――――――→ |
|---|---|---|---|---|---|---|---|---|---|---|---|---|---|---|
| CAG | GCG | TGG | GAC | AGC | GGC | ACT | GCG | GTT | TTC | GGC | GGG | GGG | ACC | AAG | CTG | ACC | GTC |
| Q | A | W | D | S | G | T | A | V | F | G | G | G | T | K | L | T | V |

| ――→ | | | | | | | | | | | | | | |
|---|---|---|---|---|---|---|---|---|---|---|---|---|---|---|
| GTG |
| L |

FG-23

| | |
|---|---|
| VH GERMLINE | DP-10/hv1051 |
| VH Family | VH1 |
| CDR3 length | 7 |
| VL Germline | 3r.9C5/DPL23 |
| VL Family | VL3 |
| CDR3 length | 9 |

TABLE 3

| ←-------------------------------- FR1 --------------------------------→ | | | | | | | | | | | | | | | | |
|---|---|---|---|---|---|---|---|---|---|---|---|---|---|---|---|---|
| CAG | GTG | CAG | CTG | GTG | CAG | TCT | GGG | GCT | GAG | GTG | AAG | AAG | CCT | GGG | TCC | TCG | GTG |
| Q | V | Q | L | V | Q | S | G | A | E | V | K | K | P | G | S | S | V |
| ←---------------------- FR1 --------------------------→ | | | | | | | | ←---------- CDR1 -----→ ← | | | | | | | |
| AAG | GTC | TCC | TGC | AAG | GCT | TCT | GGA | GGC | AAC | TTC | AGC | AGC | TAT | GCT | ATC | AGC | TGG |
| K | V | S | C | K | A | S | G | G | T | F | S | S | Y | A | I | S | W |
| ←---------------- FR2 ----------------→ | | | | | | | | ←---------------------- | | | | | | | |
| GTG | CGA | CAG | GCC | CCT | GGA | CAA | GGG | CTT | GAG | TGG | ATG | GGA | GGG | ATC | ATC | CCT | ATC |
| V | R | Q | A | P | G | Q | G | L | E | W | M | G | G | I | I | P | I |
| ----------- CRD2 ------------→ | | | | | | | | ←---------------------- | | | | | | | |
| TTT | GGT | ACA | GCA | AAC | TAC | GCA | CAG | AAG | TTC | CAG | GGC | AGA | GTC | ACG | ATT | ACC | GCG |
| F | G | T | A | N | Y | A | Q | K | F | Q | G | R | V | T | I | T | A |
| ←-------------------------------- FR3 --------------------------------→ | | | | | | | | | | | | | | | | |
| GAC | GAA | TCC | ACG | AGC | ACA | GCC | TAC | ATG | GAG | CTG | AGC | AGC | GTG | AGA | TCT | GAG | GAC |
| D | E | S | T | S | T | A | Y | M | E | L | S | S | L | R | S | E | D |
| ---------------------------→ | | | | ←------ CDR3 -----→ | | | | ←-------------- FR4 --------- | | | | | | | |
| ACG | GCC | GTG | TAT | TAC | TGT | GCG | AGG | CCC | TAT | TTG | GGC | TGG | GGC | CAA | GGG | ACA | ATG |
| T | A | V | Y | Y | C | A | R | P | Y | L | G | W | G | Q | G | T | M |
| ------------------→ | | | ←---------------------- Interchain linker ---------------------- | | | | | | | | | | | | | |
| GTC | ACC | GTC | TCT | TCA | GGT | GGC | GGC | GGT | TCC | GGA | GGT | GGT | GGT | TCT | GGC | GGT | GGT |
| V | T | V | S | S | G | G | G | G | S | G | G | G | G | S | G | G | G |
| ---------→ | ←------ VL ------------------------------- FR1--------------------------------- | | | | | | | | | | | | | | | |
| GGC | AGC | AAT | TTT | ATG | CTG | ACT | CAG | CCC | CAC | TCT | GTG | TCG | GAG | TCT | CCG | GGG | AAG |
| G | S | N | F | M | L | T | Q | P | H | S | V | S | E | S | P | G | K |
| ----------------------------→ | | | | | ←------------------------ CDR1------------------------ | | | | | | | | | | |
| ACG | GTA | AAC | ATC | TCC | TGC | ACC | CGC | AGC | AGT | GGC | AGC | ATT | GCC | AGC | CAC | TAC | GTG |
| T | V | N | I | S | C | T | R | S | S | G | S | I | A | S | H | Y | V |
| --→ | ←---------------------------- FR2 ------------------------→ | | | | | | | ←---------------------- | | | | | | | |
| CAG | TGG | TTC | CAG | CAG | CGC | CCG | GGC | AGT | GCC | CCC | GCC | ACT | GTG | ATC | TAT | GAG | GAT |
| Q | W | F | Q | Q | R | P | G | S | A | P | A | T | V | I | Y | E | D |
| ---- CDR2 -----------→ | | | | ←---------------------------- | | | | | | | | | | | | |
| AAA | CAA | AGA | CCC | TCT | GGG | GTC | CCT | GAT | CGG | TTC | TCT | GGC | TCC | ATC | GAC | AGC | TCC |
| K | Q | R | P | S | G | V | P | D | R | F | S | G | S | I | D | S | S |
| ←---------------------------- FR3 ----------------------------→ | | | | | | | | | | | | | | | | |
| TCC | AAC | TCT | GCC | TCC | CTC | ACC | ATC | TCT | GGA | CTG | AGG | ACT | GAA | GAC | GAG | GCT | GAC |
| S | N | S | A | S | L | T | I | S | G | L | R | T | E | D | E | A | D |
| ------------→ | ←-------------- CDR3 -------------------→ | | | | | | ←------ FR4 ---------------- | | | | | | | |
| TAC | TAC | TGC | CAG | TCT | TAT | GAT | ACC | GGC | ACT | TGG | GTG | TTC | GGC | GGA | GGG | ACC | AAG |
| Y | Y | C | Q | S | Y | D | T | G | T | W | V | F | G | G | G | T | K |
| --------------------→ | | | | | | | | | | | | | | | | |
| CTG | ACT | GTC | CTG | | | | | | | | | | | | | | |
| L | T | V | L | | | | | | | | | | | | | | |

FG-47  
VH Germline    DP-10/hv1051  
VH Family      VH1  
CDR3 length    4  
VL Germline    6a.366F5/V1-22  
VL Family      VL6  
CDR3 length    9

Another method of generating such an antibody is by using hybridoma mRNA or splenic mRNA as a template for PCR amplification of such genes [Huse, et al., *Science* 246:1276 (1989)]. For example, antibodies can be derived from murine monoclonal hybridomas [Richardson J. H., et al., *Proc Natl Acad Sci USA* Vol. 92:3137-3141 (1995); Biocca S., et al., *Biochem and Biophys Res Comm*, 197:422-427 (1993) Mhashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines. [Marasco, W. A., et al., *Proc Natl Acad Sci USA*, 90:7889-7893 (1993); Chen, S. Y., et al., *Proc Natl Acad Sci USA* 91:5932-5936 (1994)].

One can readily screen an antibody to insure that it has a sufficient binding affinity for the antigen of interest. The binding affinity ($K_d$) should be at least about $10^{-7}$ l/mol, more preferably at least about $10^{-8}$ l/mol.

For example, cDNA clone encoding LMP1 or a fragment thereof may be expressed in a host using standard techniques such that 5-20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, ion exchange hydrophobic, size exclusion, or affinity chromatography.

Once the protein immunogen is prepared, mice can be immunized twice intraperitoneally with approximately 50 micrograms of LMP1 protein or a fragment thereof immunogen per mouse. Sera from such immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active LMP1 antibodies according to the invention can be sacrificed three days later and their spleens removed for fusion and hybridoma production. Positive supernatants of such hybridomas can be identified using the assays described above and by, for example, Western blot analysis.

To further improve the likelihood of producing a LMP1 specific antibody, the amino acid sequence of the polypeptide encoded by a eukaryotic nucleotide sequence of LMP1 protein may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

Another method for preparing anti-LMP antibodies is by in vitro immunization techniques, such as using spleen cells, e.g., a culture of murine spleen cells, injecting an antigen, and then screening for an antibody produced to said antigen. With this method, as little as 0.1 micrograms of LMP antigen (such as the LMP proteoliposome) can be used, although about 1 microgram/milliliter is preferred. For in vitro immunization, spleen cells are harvested, for example, mice spleen cells, and incubated at the desired amount, for example, $1 \times 10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27-33 (1986)], *Salmonella typhimurium* mitogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841-845 (1984); Borrebaeck, C. A. K., *J. Immunol.* 136:3710-3715 (1986)] or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore Corp. The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find anti-LMP1 antibodies of interest. Cultures containing the anti-LMP1 antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186-187 (1993)].

This latter technique requires less antigen than the in vivo immunization because the in vivo method typically requires about 50 micrograms of antigen per mouse per injection and there are usually two boosts following primary immunization for the in vivo method.

Using any of these antibodies, one can construct $V_H$ and $V_L$ genes. For instance, one can create $V_H$ and $V_L$ libraries from murine spleen cells that have been immunized either by the above-described in vitro immunization technique or by conventional in vivo immunization and from hybridoma cell lines that have already been produced or are commercially available. One can also use commercially available $V_H$ and $V_L$ libraries. One method involves using the spleen cells to obtain mRNA which is used to synthesize cDNA. Double stranded cDNA can be made by using PCR to amplify the variable region with a degenative N terminal V region primer and a J region primer or with $V_H$ family specific primers, e.g., mouse-12, human-7.

For example, the genes of the $V_H$ and $V_L$ domains of the desired antibody such as one to LMP1 can be clone and sequenced. The first strand cDNA can be synthesized from, for example, total RNA by using oligo dT priming and the Moloney murine leukemia virus reverse transcriptase according to known procedures. This first strand cDNA is then used to perform PCR reactions. One would use typical PCR conditions, for example, 25 to 30 cycles using e.g. Vent polymerase to amplify the cDNA of the immunoglobulin genes. DNA sequence analysis is then performed. [Sanger, et al., *Proc. Natl. Acad. Sci. USA* 79:5463-5467 (1977)].

Both heavy chain primer pairs and light chain primer pairs can be produced by this methodology. One preferably inserts convenient restriction sites into the primers to make cloning easier.

Thereafter, the variable region is chosen. This is then added to the "humanized" framework motif by standard techniques.

Anti-LMP antibodies of the present invention can be detected by appropriate assays, e.g., conventional types of immunoassays. For example, a sandwich assay can be performed in which LMP protein or a fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluorescent molecules (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art. The desired antibodies and genes and primers encoding such antibodies can be packaged in kits. The other components in the kit will depend upon the use to which the kit is designed. These other components can include coupling moieties, vectors, polymerase, etc.

Another embodiment of the present invention provides chimeric receptor genes suitable for endowing lymphocytes with antibody-type specificity to LMP. Chimeric receptor genes allow one to combine the advantage of the antibody's specificity with the homing, tissue penetration, cytokine production and target-cell destruction of T lymphocytes and to extend, by ex vivo genetic manipulations, the spectrum of anti-tumor specificity of T cells. Such chimeric genes are sometimes referred to as chimeric receptor genes or chimeric genes or T-bodies. Such chimeric genes are described for example in U.S. patent application Ser. No. 08/547,263, filed Oct. 24, 1995.

The chimeric receptor genes comprise a first segment encoding at least the heavy chain binding region of an antibody (e.g., a dAb, a scFv) and a second receptor or co-receptor chain, such as a segment encoding an immune cell-triggering molecule. Preferably, the first segment encodes both the heavy and the chain binding regions.

The first segment of the chimeric gene encoding at least the heavy chain binding region of an antibody functions as the antigen recognition unit of chimeric molecules. Any heavy chain binding region of an antibody which confers LMP-specific binding can be used. In one preferred embodiment, the heavy chain binding region are scFvs.

The second segment of the chimeric gene, encoding an immune cell-triggering molecule, is preferably composed of the transmembrane and cytoplasmic domains of receptor molecules of immune cells, such as T cells and natural killer (NK) cells. Such receptors can be single or multi-chain in nature and not necessarily belong to the Ig gene superfamily. Candidate molecules for immune cell-triggering molecule are receptor molecules which take part in signal transduction as an essential component of a receptor complex, such as receptors which trigger T cells and NK activation and/or proliferation. In one embodiment the cytoplasmic domain can be deleted. However, it is preferable to have both the transmembrane and cytoplasmic domain present. Examples of triggers of T cells are subunits of the TCR, such as the α, β, γ, and δ chains of the TCR, or any of the polypeptides constituting the CD3 complex which are involved in the signal transduction, e.g., the .gamma., .delta., .epsilon., .zeta. and .eta. CD3 chains. Among the polypeptides of the TCR/CD3 (the principal triggering receptor complex of T cells), especially promising are the zeta and its eta isoform chain, which appear as either homo- or hetero-S-S-linked dimers, and are responsible for mediating at least a fraction of the cellular activation programs triggered by the TCR recognition of ligand [Weissman et al., EMBO J. 8:3651-6 (1989); Bauer et al., Proc. Natl. Acad. Sci. USA 88:3842-6 (1991)]. These polypeptides have very short extracellular domains which can serve for the attachment of a binding domain such as the scFv.

Additional examples of immune cell trigger molecules are any one of the IL-2 receptor (IL-2R) p55 (.alpha.) or p75 (.beta.) or .gamma. chains, especially the p75 and .gamma. subunits which are responsible for signaling T cell and NK proliferation.

Further candidate receptor molecules for creation of chimera receptor genes in accordance with the present invention include the subunit chains of Fc receptors.

In the group of NK-stimulatory receptors the most attractive candidates are the .gamma.- and CD16.alpha.-subunits of the low affinity receptor for IgG, Fc.gamma.RIII. Occupancy or cross-linking of Fc.gamma.RIII (either by anti-CD16 or through immune complexes) activates NK cells for cytokine production, expression of surface molecules and cytolytic activity [Unkeless, J. C. et al. Annu. Rev. Immunol. 6:251-281 (1988); Ravetch, J. V. and Kinet, J.-P. Annu. Rev. Immunol. 9:457-492 (1991)]. In NK cells, macrophages, and B and T cells, the Fc.gamma.RIII appears as a heterooligomeric complex consisting of a ligand-binding .alpha. chain associated with a disulfide-linked .gamma. or zeta chain. The Fc.gamma.RIIIA signalling gamma chain [Wirthmuller, U. et al. J. Exp. Med. 175:1381-1390 (1992); Lanier, L. G. et al. J. Immunol. 146:1571-1576 (1991); Vivier, E. et al. J. Immunol. 147:4263-4270 (1991)] serves also as part of the Fc.epsilon.RI complex, where it appears as a homodimer, is very similar to the CD3 zeta chain, and in fact can form heterodimers with it in some cytolytic T lymphocytes (CTL) and NK cells [Orloff, D. G. et al. Nature (London) 347:189-191 (1990). Chimeras between these polypeptides and the CD4 [Romeo, C. and Seed, B. Cell 64:1037-1046 (1991)], the CD8 [Irving, B. A. and Weiss, A. Cell 64:891-901 (1991)], IL-2 receptor chain [Letourneur, F. and Klausner, R. D. Proc. Natl. Acad. Sci. USA 88:8905-8909 (1991)] or CD16 extracellular domains, can be active in signalling T cell stimulation even in the absence of other TCR/CD3 components.

Other lymphocyte accessory and adhesion molecules can be used such as CD2 and CD28, which transduce a co-stimulatory signal for T-cell activation.

Preferably, desirable immune cell trigger molecules have the ability to be expressed autonomously (i.e., as a single chain), the ability to be fused to an extracellular domain such that the resultant chimera is expressed on the surface of an immune cell into which the corresponding gene was genetically introduced, and the ability to take part in signal transduction programs secondary to encounter with a target ligand.

The binding region segment is joined to the immune cell triggering segment so the antibody portion will be extracellular when the chimera is expressed. This is accomplished by known means, such as joining the antibody segment either to the very end of the transmembrane portion opposite the cytoplasmic domain of the trigger molecule or by using a spacer which is either part of the endogenous extracellular portion of the triggering molecule or from other sources. The chimeric molecules of the present invention have the ability to confer on the immune cells on which they are expressed MHC non-restricted antibody-type specificity. Thus, a continuous polypeptide of antigen binding and signal transducing properties can be produced and utilized as a targeting receptor on immune cells.

These cells can be prepared ex vivo, amplified and then reintroduced into a subject by known methods such as I.V. administration, subcutaneous administration, in the form of capsules, liposomes, etc. In vivo, cells expressing these genetically engineered chimeric receptors will home to their target, stimulated by it to attract other effector cells, or, by itself, will mediate specific destruction of the target cells.

In a preferred embodiment, the target cells are EBV infected cells expressing LMP and the antibody binding domain is derived from an antibody specific to an epitope expressed on the tumor cells. It is expected that such cytolysis can also be independent of exogenous supply of IL-2, thus providing a specific and safer means for adoptive immunotherapy.

In preferred embodiments, the immune cells are T-cells or NK-cells. The antibody design of the present invention will thus involve retargeting lymphocytes in vivo in an MHC-non-restricted manner. Thus, the T-cells can be re-targeted in vivo to EBV infected cells.

Current methods of administering such transformed cells include adoptive immunotherapy or cell-transfer therapy. These methods allow the return of the transformed immune system cells to the blood stream. Rosenberg, S. A., Scientific American 62 (May 1990); Rosenberg et al., The New England Journal of Medicine 323(9):570 (1990).

The invention also provides expression vectors comprising said chimeric genes and to lymphocytes transformed with said expression vectors. Various types of lymphocyte cells are suitable, for example, natural killer cells, cytotoxic T cells, helper T cells, suppressor T cells, lymphokine activated cells, subtypes thereof and any other cell type which can express chimeric receptor chain. The transformed cells of the present invention may be administered in the form of a pharmaceutical composition with suitable pharmaceutically acceptable excipients. Such compositions may be administered to any animal which may experience the beneficial effects of the transformed cell of the present invention, including humans.

The chimeric receptor genes can confer on the lymphocytes the following functions: antibody-type specificity toward the predefined LMP antigen; specific "homing" to their targets; specific recognition, activation, and execution of effector function as a result of encountering the target; and specific and controlled proliferation at the target site. Using an antibody can permit controlled and selective blocking of the aforementioned functions using soluble haptens or Fab' of anti-idiotypic antibodies.

Candidate immune cells to be endowed with antibody specificity using this approach are: NK cells, lymphokine-activated killer cells (LAK), cytotoxic T cells, helper T cells, and the various subtypes of the above. These cells can execute their authentic natural function and also act as carriers of foreign genes designated for gene therapy, and the chimeric receptor shall serve in this case to direct the cells to their target. This approach can be applied also to anti-idiotypic vaccination by using helper T cells expressing chimeric receptors made of Fv of antiidiotypic antibodies. Such "designer lymphocytes" will interact and stimulate idiotype-bearing B cells to produce antigen-specific antibodies, thus bypassing the need for active immunization with toxic antigens.

The antibodies of the present invention can be expressed by a vector containing a DNA segment encoding the single chain antibody described above.

These can include vectors, liposomes, naked DNA, adjuvant-assisted DNA, gene gun, catheters, etc. as discussed above.

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, and viral vectors.

The vector can be employed to target essentially any desired target cell, such as a glioma. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of LMP1 protein in a sample.

In one preferred embodiment, the antibody can also be used to bind to and disrupt an LMP, such as an LMP1 interaction. It would be administered as described earlier.

The antibody cassette is delivered to the cell by any of the known means. For example, a cassette containing these antibody genes, such as the scFv gene, can be targeted to a particular cell by a number of techniques as described above.

Preferably the vectors of the present invention use internal ribosome entry site (IRES) sequences to force expression of the desired gene, for example, an scFv. In another embodiment, one can use an IRES to force a stoichiometric expression of light chain and heavy chain. This forced expression avoids the problem of "silencing" where cells expressing the desired protein are phenotypically not seen, which may occur with a wide range of gene products. Another embodiment comprises using the IRES sequences the single chain antibodies to the target of interest can be linked with a selectable marker. Selectable markers are well known in the art, e.g., genes that express protein that change the sensitivity of a cell to stimuli such as a nutrient, an antibiotic, etc. Examples of these genes include neo puro, tk, multiple drug resistance (MDR), etc.

The resultant products of that IRES linkage are not fusion proteins, and they exhibit their normal biological function. Accordingly, the use of these vectors permits the forced expression of a desired protein. Intracellular immunization strategies that are aimed at inhibiting target gene expression can be RNA (antisense, ribozymes, RNA decoys) or protein (antibodies expressed intracellularly, antibodies delivered to a cell which then enters the cell, dominant-negative mutants) based and each group of inhibitors has advantages and limitations.

One preferred method of treating EBV infected cells is to deliver antibodies to EBV infected cells. This can be done by delivering the already expressed antibody to the cell or by having the antibody expressed within the cell. The antibody will also have an intracellular localization sequence, preferably one directed to the Golgi apparatus or the endoplasmic reticulum such as KDEL. These antibodies will then target LMP proteins as they are being processed in the EBV infected cells and inhibit malignant transformation by silencing an LMP function such as LMP1 resulting in phenotypic and functional knockout. See U.S. Pat. Nos. 5,965,371, 6,004, 940, 6,072,036.

Using any suitable technique known in the art, such as Northern blotting, quantitative PCR, etc. the level of the LMP protein or mRNA in cells, particularly in potentially malignant cells such as prostate cells, can be measured. An increase in the level of expression of LMP1 is associated with malignancy or susceptibility for malignancy.

Alternatively, the antibodies of the invention can be used in standard techniques such as Western blotting or immunohistochemistry to detect the presence of cells expressing LMP, to quantify the level of expression. Preferably, one uses FACS analyses. In this way, the antibodies can be used diagnostically and prognostically.

In another embodiment, the invention can be used in passive immunotherapy. Preferably, as a whole IgG molecule. Alternatively, one can use a complex comprising an antibody, preferably a scFv, or antibody fragment directed against an immunogenic fragment of a LMP protein linked to a cytotoxic molecule. Various immunoconjugates in which antibodies were used to target chemotherapeutic drugs (P. N. Kularni, A. H. Blair, T. I. Ghose, Cancer Res. 41, 2700 (1981); R. Arnon, R. and M. Sela, Immunol. Rev. 62, 5 (1982); H. M. Yang and R. A. Resifeld, Proc. Natl. Acad. Sci. U.S.A., 85, 1189 (1988); R. O. Dilman, D. E. Johnson, D. L. Shawler, J. A. Koziol, Cancer Res. 48, 6097 (1988); L. B. Shih, R. M. Sharkey, F. J. Primus, D. M. Goldenberg, Int. J. Cancer 41, 832 (1988); P. A. Trail, et al., Cancer Res. 52, 5693 (1992)), or plant and bacterial toxins (I. Pastan, M. C. Willingham, D. J. Fitzgerald, Cell 47, 641 (1986); D. D. Blakey, E. J. Wawrzynczak, P. M. Wallace, P. E. Thorpe, in Monoclonal Antibody Therapy Prog. Allergy, H. Waldmann, Ed. (Karger, Basel, 1988), pp. 50-90) have been evaluated in preclinical models and found to be active in vitro and in vivo. U.S. Pat. No. 5,869,045 describes in detail how to make such antibody conjugates and is hereby incorporated as reference in its entirety.

Examples of therapeutic agents that can be conjugated with anti-LMP antibodies include, but are not limited to, antimetabolites, alkylating agents, anthracyclines, and antimitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antimitotic agents include vincristine and vinblastine (which are commonly referred to as vinca alkaloids). Other cytotoxic agents include procarbazine, hydroxyurea, asparaginase, corticosteroids, mytotane (O,P'-(DDD)), and interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid. Clearly analogs and homologs of such therapeutic and cytotoxic agents are encompassed by the present invention. For example, the chemotherapeutic agent aminopterin has a correlative improved analog namely methotrexate. Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

The invention is further directed to methods for detection of the expression of LMP or a derivative thereof in a biological sample using antibodies to an LMP, such as LMP1. Such antibodies can be used for diagnosis and/or prognostics as well as for treatment of individuals affected with EBV. The LMP antigens of the invention can be used to elicit immune responses, for example in a vaccine, to prevent EBV infection in individuals.

The nucleic acid encoding an LMP antigen or fragments thereof can be expressed by any known means. These include creating an expression cassette (nucleic acid construct), where the nucleic acid is operably linked to a promoter. Other enhancing elements are known and may also be used. The codons used to synthesize the protein of interest may be optimized, converting them to codons that are preferentially used in mammalian cells. Optimal codons for expression of proteins in non-mammalian cells are also known, and can be used when the host cell is a non-mammalian cell (for example, insect cells, yeast cells, bacteria).

The nucleic acid construct encoding LMP or fragments thereof created as described above can be introduced into a cell for the expression by known means. These include, for example, vectors, liposomes, naked DNA, adjuvant-assisted DNA, gene gun, catheters, etc. Vectors include chemical conjugates, plasmids, phage, etc. The vectors can be chromosomal, non-chromosomal or synthetic. Commercial expression vectors are well known in the art, for example pcDNA 3.1, pcDNA4 HisMax, pACH, pMT4, PND, etc. Promoters that can be used to express the gene are well known in the art. The promoters chosen are selected based upon the host cell which the protein is expressed in. These include cytomegalovirus (CMV) intermediate early promoter, a viral LTR such as the Rous sarcoma virus LTR, HIV-LTR, HTLV-1 LTR, the simian virus 40 (SV40) early promoter, E. coli lac V5 promoter and the herpes simplex TK virus promoter.

Preferred vectors include viral vectors, fusion proteins and chemical conjugates. Retroviral vectors include Moloney murine leukemia viruses. Other vectors include pox vectors such as orthopox or avipox vectors, herpesvirus vectors such as a herpes simplex I virus (HSV) vector (Geller, A. I. et al., (1995), *J. Neurochem,* 64: 487; Lim, F., et al., (1995) in *DNA Cloning: Mammalian Systems*, D. Glover, Ed., Oxford Univ. Press, Oxford England; Geller, A. I. et al. (1993), *Proc Natl. Acad. Sci.*: U.S.A. 90:7603; Geller, A. I., et al., (1990) *Proc Natl. Acad. Sci USA* 87:1149), adenovirus vectors (LeGal LaSalle et al. (1993), *Science,* 259:988; Davidson, et al. (1993) *Nat. Genet* 3: 219; Yang, et al., (1995) *J. Virol.* 69: 2004) and adeno-associated virus vectors (Kaplitt, M. G., et al. (1994) *Nat. Genet.* 8: 148). The particular vector chosen will depend upon the host cell used.

The introduction of the LMP nucleic acid construct into the host cell can be by standard techniques, e.g. infection, transfection, transduction or transformation. Examples of modes of gene transfer include e.g., naked DNA, CaPO4 precipitation, DEAE dextran, electroporation, protoplast fusion, lipofection, cell microinjection, and viral vectors.

An antigenic tag sequence may be inserted in the LMP protein to assist in its purification and in orienting the protein on the solid surface. Preferably, the tag sequence is present at either the N-terminal end or the C-terminal end of the protein. The tag is preferably 6 to 15 amino acids in length, still more preferably about 6 to 9 amino acids. The tag is selected and its coding sequence inserted into the gene encoding the protein in a manner not to affect the overall conformation or function of the protein. Tags can include HA, polyoma, C9, FLAG, etc.

Doses of the pharmaceutical compositions will vary depending upon the subject and upon the particular route of administration used. Dosages can range from 0.1 to 100,000 µg/kg a day, more preferably 1 to 10,000 µg/kg.

Routes of administration include oral, parenteral, rectal, intravaginal, topical, nasal, direct injection, etc.

An exemplary pharmaceutical composition is a therapeutically effective amount of an oligomer, antibody etc., that recognizes the EBV infected cells, or that can induce an immune reaction against EBV infected cells, thereby acting as a prophylactic immunogen, optionally included in a pharmaceutically-acceptable and compatible carrier. The term "pharmaceutically-acceptable and compatible carrier" as used herein, and described more fully below, includes one or more compatible solid or liquid filler diluents or encapsulating substances that are suitable for administration to a human or other animal. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

In one preferred method of immunization one would prime with a proteoliposome containing LMP1 antigen, comprising at least one of the extracellular loops of LMP1, and then boost one or more times with an LMP1 proteoliposome comprising all three of the extracellular loops encoded by amino acids 1-207.

One can prepare kits containing the proteoliposome containing an LMP, such as LMP1 or LMP2A or LMP2B. The kits would contain the LMP proteoliposome in sterile and pyrogen free containers. Doses of the pharmaceutical compositions of the invention (e.g. the LMP proteoliposome or an antibody to LMP) will vary depending on the subject and upon the particular route of administration used. Dosages can range from 0.1 to 100,000 µg/kg per day, more preferably 1 to 10,000 µg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. In the embodiment where the prime is the proteoliposome containing the extracellular loop of an LMP1, with the boost of proteoliposomes containing LMP1 and native LMP2A or B, it is presently preferred to have a series of at least 2 boosts, preferably 3 to 5 boosts spread out over a year. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at 1442-43. (e.g., Hepatitis B Vaccine-type protocol); (ii) for example with other vaccines the recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, *Physician's Desk Reference*, Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

EXAMPLE

Formation of ΔTES-C9 Proteoliposomes.

Paramagnetic proteoliposomes containing a truncated form of LMP1 (ΔTES, aa 1-207) were obtained. The mutant contains the cytoplasmic N-terminus, the six transmembrane domains and 20 aa of the C-terminal tail of LMP1; it also contains a C-terminal nonapeptide (C9) tag, recognized by the 1D4 monoclonal antibody. The protein was expressed in COS-7 cells. COS-7 cells were transfected as described. $10^8$ cells were then lysed in 10 ml of solubilization buffer for 30 min at 4° C. Cell debris was removed and the cleared lysate incubated with $2 \times 10^8$ 1D4-streptavidin-coated beads for 4 h at 4° C. on a rocking platform.

Paramagnetic beads were conjugated with 1D4 and streptavidin and used to capture the mutant ΔTES-C9 from the cell lysate. The beads were than mixed with solubilised lipids containing biotynil-DOPE, that self-assemble around the beads producing the lipid bilayer.

Protein Composition of ΔTES-C9 Proteoliposomes.

The protein composition of ΔTES proteoliposomes were analyzed. COS-7 cells expressing ΔTES were labeled with [$^{35}$S]methionine and [$^{35}$S]cysteine and used to produce proteoliposomes. For this purpose, proteoliposomes were obtained from [$^{35}$S]methionine and [$^{35}$S]cysteine labeled cells, incubated for 1 h at 55° C. in 2% SDS buffer and the eluted protein was run on an 11% SDS gel. The gel was treated in Enhancer, dried and autoradiographed. The labeled protein incorporated in the proteoliposomes were then analyzed on polyacrylamide gel. The band corresponding of ΔTES (24 KDa) was observed, while other cellular proteins were not present.

Panning of a Phage Library with ΔTES-C9 Proteoliposomes.

The ΔTES-C9 proteoliposomes were used to select recombinant antibodies from a human single-chain antibody phage display library of approximately $1.5 \times 10^{10}$ members. The selection was performed essentially as described in "Screening of phage antibody libraries", Meth in Enzimology, Vol 267, 83-109. Approximately $5 \times 10^7$ proteoliposomes were blocked for 1 h at room temperature, with 4% milk and 1/500 Megablock in PBS. $2 \times 10^{13}$ t.u. of phages was added and the mixture of phages and proteoliposomes was gently rotated for 1 h at room temperature. Proteoliposomes and captured phages were washed 12 times, and the phages were eluted by 100 mM Gly-HCl pH 2.2 and neutralized.

Half of the eluted phages was used to infect 10 ml log phase *E. coli* TG1 which were plated on GTY-AMP-Glu plates.

Each round of selection was performed using approximately $5 \times 10^7$ proteoliposomes; in the first round $2 \times 10^{13}$ t.u. of phages were used and the output was 105 t.u./ml. After the fourth round the output was $5 \times 10^7$ t.u./ml.

After the fourth round of panning, 48 of the selected individual phages were tested for ability to bind BJAB-WT4 cells relative to binding of BJAB cells using a cell-based ELISA.

The titer of the captured phages increased from 105 to $5 \times 10^7$ from the second to the fourth round of panning. All resulted positive in the cell-based ELISA assay.

Fingerprinting and Sequencing.

The 48 positive clones were analyzed by fingerprinting. PCR analysis showed the presence of the 800 bp insert, corresponding to the scFv, in all the clones. Amplification was carried out for 25 cycles at 94° for 30 sec. 58° for 30 sec, 72° for 1.5 min. 800 bp PCR products were digested using BstNI restriction enzyme and visualized on a 2% agarose gel. Based on restriction analysis the 48 clones can be classified into 6 groups. Sequence analysis showed the presence of 3 unique scFvs.

Cell Lines and Plasmids.

COS-7 and 293 are human embryonal kidney cell lines. CF2 is a canine cell line. BJAB is an EBV negative Burkitt's lymphoma cell line. BJAB-WT4 is an LCL transformed by a recombinant EBV carrying a N-terminal Flag-tagged LMP1. pC9-LMP1 is a pSG5-based plasmid, expressing a N-terminal C9-Tagged LMP1. pΔTES-C9 is a pSG5-based plasmid, expressing a truncated form (aa 1-207) of LMP1, with a C-terminal C9 tag.

Transfection and Radiolabeling.

293, cos7 and CF2 cells were cultured in Dulbecco's modified Eagle's medium supplemented with 10% fetal calf serum. For the transient transfection cells were plated on 150 mm dishes and the following day were transfected with plasmids expressing C9-LMP1 or ΔTES-C9, by using Gene Porter Reagent (Gene Therapy System, San Diego, Calif.).

After 24 h the medium was replaced with 8 ml/dish of methionine/cysteine free DMEM containing 400 µCi each of [$^{35}$S]methionine and [$^{35}$S]cysteine. Labeled cells were harvested with 5 mM EDTA in PBS, pelleted and frozen.

Immunoprecipitation.

Approximately $10^7$ cells were lysed in 1 ml of solubilization buffer (100 mM $(NH_4)_2SO_4$, 20 mM Tris-HCl pH 7.5, 10% glycerol, 1% w/V Cymal-5 and Protease Inhibitor Mixture) for 30 min at 4° C. Cell debris was removed by centrifugation, 15 min at 14,000×g and cleared cell lysates were incubated with anti-C9 Sepharose beads for 2 h at 4° C. on a rocking platform. Beads were than washed 8 times in solubilization buffer and bound proteins were recovered by incubation in 2% SDS buffer for 1 h at 55° C. Eluted proteins were separated on a 12% or 15% SDS-PAGE mini-gel. The gel was incubated for 1 h with Enhancer solution, dried and autoradiographed.

Coating of Dynabeads M-280 by Antibodies and Streptavidin

The protocol was already described (Mirzabekov et al 2000), briefly: $6 \times 10^8$ tosyl-activated Dynabeads M-280 (Dynal, Inc) were conjugated with 1 mg of 1D4 antibodies (National Cell Colture Centre, Minneapolis) and 40 µg of streptavidin by a 20 hours incubation at 37° C. The non-covalented bound proteins were removed by incubation in 1% Cymal-5, 20 mM Tris-HCl pH 7.5, 100 mM $(NH_4)_2SO_4$, 1 mM NaCl. The efficiency of antibody conjugation was checked by FACS using anti-mouse R-phycoerythrin-conjugated IgG (Boheringer Mannheim).

Optimization of Magnetic Bead/Cell Number Ratio

To optimize the cell/bead ratio for the formation of proteoliposomes, cos7 cells were transfected with ΔTES-C9, radiolabeled and lysed as describe above. The cleared lysates derived from approximately $10^7$ cells were incubated with $10^6$, $3 \times 10^6$, $10^7$, $3 \times 10^7$, $5 \times 10^7$, $7 \times 10^7$, $1 \times 10^8$, $3 \times 10^8$ 1D4-streptavidin-coated beads for 3 h at 4° C. on a rocking platform. Beads were than washed several times and incubated at 55° C. for 1 h. The eluted proteins were run on a SDS-PAGE gel and visualized by autoradiography.

Analysis of the Protein Composition in ΔTES-C9 Proteoliposomes

The protein composition of ΔTES-C9 proteoliposomes was tested by autoradiography.

All references described herein are specifically incorporated herein by reference. Those skilled in the art recognize that based upon the disclosure and using routine experimentation equivalents to the specific embodiments can be obtained and are part of the invention as claimed.

We claim:

1. An antibody fragment that binds to an extracellular epitope of an Epstein Barr Virus (EBV) latent membrane protein 1 (LMP1), wherein the antibody fragment has an amino acid sequence comprising an amino acid sequence selected from the group consisting of SEQ ID NO.: 3, SEQ ID NO.: 5, and SEQ ID NO.: 7.

2. An isolated antibody or antibody fragment that specifically binds to an extracellular epitope of an EBV LMP 1, wherein the antibody or antibody fragment comprises:

a VH CDR1 consisting of amino acids 31-35 of SEQ ID NO:3, a VH CDR2 consisting of amino acids 50-66 of SEQ ID NO:3, a VH CDR3 consisting of amino acids 99-105 of SEQ ID NO:3, a VL CDR1 consisting of amino acids 154-164 of SEQ ID NO:3, a VL CDR2 consisting of amino acids 180-186 of SEQ ID NO:3, and a VL CDR3 consisting of amino acids 219-227 of SEQ ID NO:3.

3. The antibody or antibody fragment of claim 2, wherein the antibody or antibody fragment is selected from the group consisting of single chain antibodies, scFv, Fab', Fab, F(ab)$_2$, humanized antibodies, human antibodies, and chimeric antibodies.

4. An isolated antibody or antibody fragment that specifically binds to an extracellular epitope of an EBV LMP 1, wherein the antibody or antibody fragment comprises:

a VH CDR1 consisting of amino acids 30-34 of SEQ ID NO:5,
a VH CDR2 consisting of amino acids 49-65 of SEQ ID NO:5,
a VH CDR3 consisting of amino acids 98-104 of SEQ ID NO:5,
a VL CDR1 consisting of amino acids 151-161 of SEQ ID NO:5,
a VL CDR2 consisting of amino acids 177-183 of SEQ ID NO:5, and
a VL CDR3 consisting of amino acids 216-224 of SEQ ID NO:5.

5. The antibody or antibody fragment of claim 4, wherein the antibody or antibody fragment is selected from the group consisting of single chain antibodies, scFv, Fab', Fab, F(ab)2, humanized antibodies, human antibodies, and chimeric antibodies.

6. An isolated antibody or antibody fragment that specifically binds to an extracellular epitope of an EBV LMP 1, wherein the antibody or antibody fragment comprises:

a VH CDR1 consisting of amino acids 31-35 of SEQ ID NO:7,
a VH CDR2 consisting of amino acids 50-66 of SEQ ID NO:7,
a VH CDR3 consisting of amino acids 99-102 of SEQ ID NO:7,
a VL CDR1 consisting of amino acids 151-163 of SEQ ID NO:7,
a VL CDR2 consisting of amino acids 179-185 of SEQ ID NO:7, and
a VL CDR3 consisting of amino acids 220-228 of SEQ ID NO:7.

7. The antibody or antibody fragment of claim 6, wherein the antibody or antibody fragment is selected from the group consisting of single chain antibodies, scFv, Fab', Fab, F(ab)2, humanized antibodies, human antibodies, and chimeric antibodies.

8. The antibody fragment of claim 1, wherein the antibody fragment has an amino acid sequence comprising the amino acid sequence of SEQ ID NO.: 3.

9. The antibody fragment of claim 1, wherein the antibody fragment has an amino acid sequence comprising the amino acid sequence of SEQ ID NO.: 5.

10. The antibody fragment of claim 1, wherein the antibody fragment has an amino acid sequence comprising the amino acid sequence of SEQ ID NO.: 7.

* * * * *